(12) United States Patent
Dickie et al.

(10) Patent No.: US 11,324,488 B2
(45) Date of Patent: May 10, 2022

(54) SYSTEMS AND METHODS OF ESTABLISHING A SECONDARY CONNECTION AT AN ULTRASOUND IMAGING MACHINE, FOR PROVIDING ACCESS TO AN ULTRASOUND IMAGE FEED

(71) Applicant: Clarius Mobile Health Corp., Burnaby (CA)

(72) Inventors: Kris Dickie, Vancouver (CA); Laurent Pelissier, North Vancouver (CA); Benjamin Eric Kerby, Richmond (CA); Trevor Stephen Hansen, North Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 227 days.

(21) Appl. No.: 16/872,312

(22) Filed: May 11, 2020

(65) Prior Publication Data
US 2020/0268359 A1    Aug. 27, 2020

Related U.S. Application Data

(63) Continuation of application No. 15/936,948, filed on Mar. 27, 2018, now Pat. No. 10,646,205.

(51) Int. Cl.
*A61B 8/00* (2006.01)
*G06K 19/06* (2006.01)
(Continued)

(52) U.S. Cl.
CPC ............ *A61B 8/565* (2013.01); *A61B 8/4438* (2013.01); *A61B 8/462* (2013.01); *G06F 3/1454* (2013.01);
(Continued)

(58) Field of Classification Search
CPC ....... A61B 8/4438; A61B 8/462; A61B 8/464; A61B 8/54; A61B 8/565; A61B 8/00;
(Continued)

(56) References Cited

U.S. PATENT DOCUMENTS 6,210,327 B1    4/2001  Brackett et al.
6,780,154 B2    8/2004  Hunt et al.
(Continued)

FOREIGN PATENT DOCUMENTS

WO         0188682 A1    11/2001
WO    2017013511 A1     1/2017

OTHER PUBLICATIONS

Banerjee, S. et al. May 2002. Scalable Application Layer Multicast. Department of Computer Science, University of Maryland.

*Primary Examiner* — Nelson M Rosario
(74) *Attorney, Agent, or Firm* — Julian Ho

(57) ABSTRACT

The present embodiments relate generally to methods for providing viewing access to an ultrasound image feed generated at an ultrasound imaging machine. A multi-use display device may form a first link-layer connection with the ultrasound image machine for transmitting commands that control imaging parameters of the ultrasound image feed. The multi-use display device may then: determine link-layer connection parameters that allow the ultrasound imaging machine to form a second link-layer connection with a receiving device (the receiving device having no link-layer connection with the ultrasound imaging machine), and provide the connection parameters to the receiving device. The ultrasound imaging machine forms a second link-layer connection with the receiving device, based the connection parameters. The second link-layer connection is then used for receiving, at the receiving device, the ultrasound image feed controlled by the multi-use display device.

20 Claims, 11 Drawing Sheets

(51) Int. Cl.
*G06K 7/14* (2006.01)
*G06K 7/10* (2006.01)
*G06F 3/14* (2006.01)

(52) U.S. Cl.
CPC ....... *G06K 7/10237* (2013.01); *G06K 7/1413* (2013.01); *G06K 19/06028* (2013.01); *G06F 2211/005* (2013.01)

(58) Field of Classification Search
CPC ......... A61B 8/4472; A61B 8/465; A61B 8/56; G06F 3/1454; G06F 2211/005; G06K 19/06028; G06K 7/10237; G06K 7/1413; G09G 5/006; G09G 2370/16; G09G 2380/08; G01N 29/24; G16H 10/40; G16H 40/20; G16H 40/67; H04B 7/24
See application file for complete search history.

(56) References Cited

U.S. PATENT DOCUMENTS

| | | | |
|---|---|---|---|
| 7,418,480 | B2 | 8/2008 | Katsman et al. |
| 10,646,205 | B2 | 5/2020 | Dickie et al. |
| 2005/0043620 | A1 | 2/2005 | Fallows et al. |
| 2006/0094959 | A1 | 5/2006 | Lin et al. |
| 2007/0113261 | A1 | 5/2007 | Roman et al. |
| 2007/0223574 | A1 | 9/2007 | Roman et al. |
| 2010/0202510 | A1 | 8/2010 | Kyle |
| 2011/0105904 | A1* | 5/2011 | Watanabe ................ A61B 8/56 600/443 |
| 2011/0249125 | A1 | 10/2011 | Wallack et al. |
| 2012/0179039 | A1 | 7/2012 | Pelissier et al. |
| 2014/0043485 | A1 | 2/2014 | Bateman et al. |
| 2014/0323869 | A1* | 10/2014 | Jin ....................... A61B 8/4472 600/459 |
| 2015/0065038 | A1 | 3/2015 | Lee et al. |
| 2015/0369915 | A1 | 12/2015 | Eibye et al. |
| 2016/0278739 | A1 | 9/2016 | Pelissier et al. |

* cited by examiner

SYSTEMS AND METHODS OF ESTABLISHING A SECONDARY CONNECTION AT AN ULTRASOUND IMAGING MACHINE, FOR PROVIDING ACCESS TO AN ULTRASOUND IMAGE FEED

CROSS-REFERENCE TO RELATED APPLICATION

This application is a continuation of U.S. patent application Ser. No. 15/936,948 entitled "SYSTEMS AND METHODS OF ESTABLISHING A SECONDARY CONNECTION AT AN ULTRASOUND IMAGING MACHINE, FOR PROVIDING ACCESS TO AN ULTRASOUND IMAGE FEED" filed Mar. 27, 2018. The entire contents of U.S. patent application Ser. No. 15/936,948 are hereby incorporated by reference.

FIELD

The present disclosure relates generally to ultrasound imaging, and in particular, systems and methods of establishing a secondary connection at an ultrasound imaging machine, for providing access to an ultrasound image feed.

BACKGROUND

Ultrasound imaging systems are a powerful tool for performing real-time, non-invasive imaging procedures in a wide range of medical applications. These systems typically include a display for showing an ultrasound image feed to an operator. In certain situations, it may be desirable to provide viewing access of the ultrasound image feed on a secondary device (called a receiving device herein). For example, the receiving device may be a larger display (e.g., a television or monitor) suitable for viewing by a larger audience. Providing viewing access may be helpful in an educational setting where multiple students can view the ultrasound image feed more easily on the receiving device.

In situations where the receiving device includes a display, some existing solutions use screen mirroring technology to provide viewing access of the ultrasound image feed. Screen mirroring may replicate the ultrasound image feed being displayed from a primary display device to a secondary display. However, screen mirroring typically requires the primary display to receive ultrasound image data, process it for display, and further transmit the ultrasound image feed to the secondary display. This places a large processing burden on the primary display device and may slow down its processing. Also, many screen mirroring services require the primary display and secondary display to be on the same local area network (LAN) to allow the primary display to discover the secondary display. This may introduce an inconvenient step of joining a LAN that needs to be performed at the secondary display prior to viewing the ultrasound image feed thereon.

There is thus a need for improved ultrasound systems and methods of establishing a secondary connection at an ultrasound imaging machine that provide access to an ultrasound image feed. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

Figure 1:
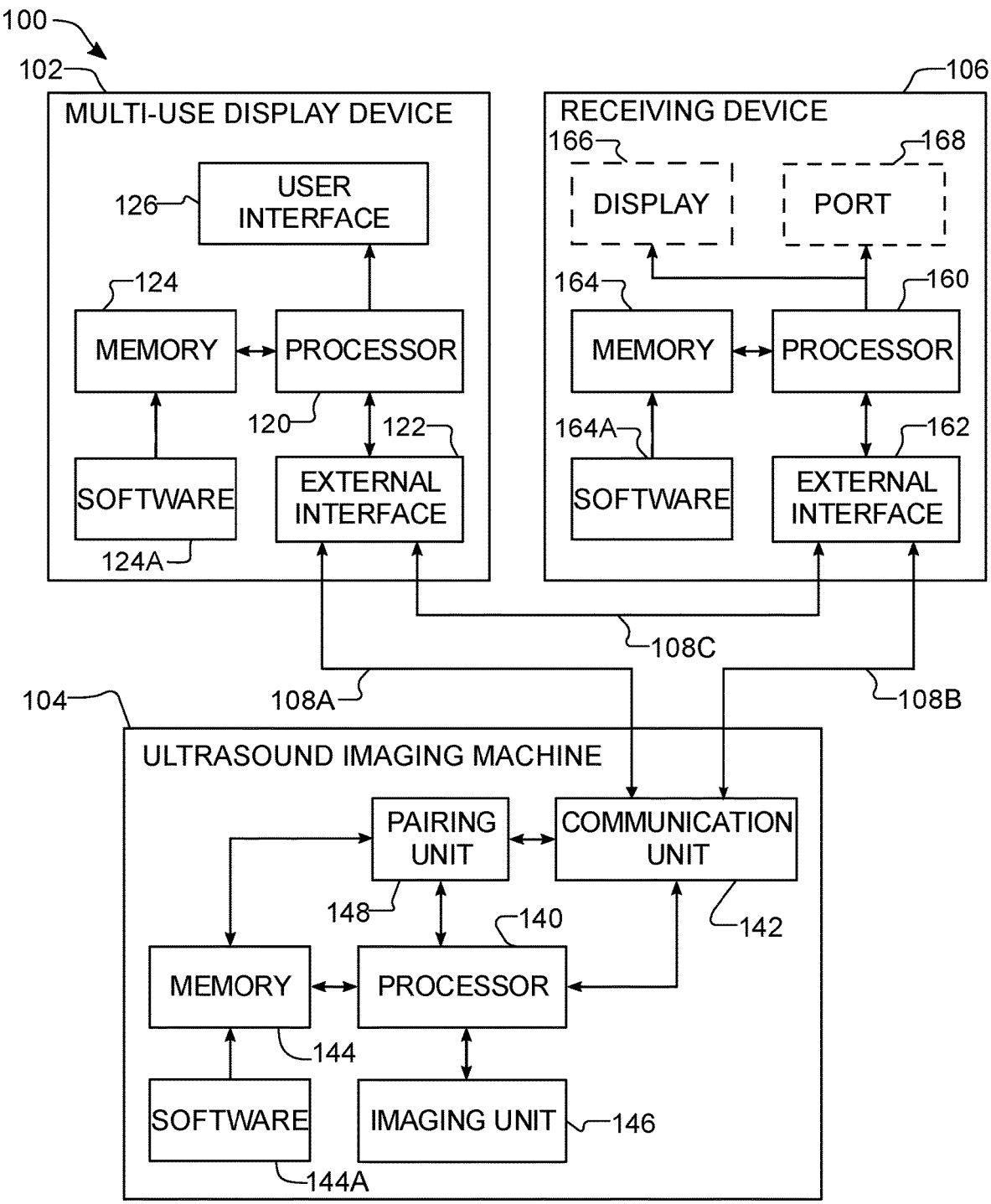
FIG. 1 shows a functional block diagram of an ultrasound system, according to at least one embodiment of the present disclosure.

In a first broad aspect of the present disclosure, there is provided a method of providing viewing access to an ultrasound image feed generated at an ultrasound imaging machine, the method comprising, at a multi-use display device: forming a first link-layer connection with the ultrasound image machine, the first link-layer connection being for transmitting commands that control imaging parameters of the ultrasound image feed; determining link-layer connection parameters that allow the ultrasound imaging machine to form a second link-layer connection with a receiving device, the receiving device having no link-layer connection with the ultrasound imaging machine; and providing the connection parameters to the receiving device, wherein the receiving device forms a second link-layer connection with the ultrasound imaging machine using the connection parameters, the second link-layer connection being used for receiving, at the receiving device, the ultrasound image feed controlled by the multi-use display device.

In some embodiments, the first link-layer connection and the second link-layer connection are each formed using a wireless local area network (WLAN) connection. In some embodiments, the connection parameters comprise: a service set identifier (SSID) associated with the WLAN, and a password for connecting to the WLAN. In some embodiments, the receiving device comprises another multi-use display device.

In some embodiments, the receiving device comprises a dongle having a port for connecting an image output device, wherein one or more ultrasound images from the ultrasound image feed received at the receiving device is provided to the image output device via the port. In some embodiments, the commands that control imaging parameters of the ultrasound image feed comprise a signal marking the one or more ultrasound images from the ultrasound image feed to be provided to the image output device via the port, and the signal is transmitted from the ultrasound imaging machine to the receiving device. In some embodiments, a signal is transmitted from the multi-use display device to the receiving device, and the signal marks the one or more ultrasound images from the ultrasound image feed to be provided to the image output device via the port.

In some embodiments, the method further comprises providing the connection parameters via an optical communication channel. In some embodiments, the optical communications channel comprises: displaying a barcode embedding the connection parameters, the barcode for reading by a barcode reader on the receiving device.

In some embodiments, the providing the connection parameters to the receiving device comprises communicating the connection parameters to the receiving device via a contactless communication channel. In some embodiments, the contactless communication channel comprises a near field communication (NFC) communication channel, and the method further comprises: configuring an NFC integrated circuit (IC) to transmit the connection parameters for reading by a NFC reader on the receiving device.

In some embodiments, the first link-layer connection is formed using a first communications protocol, and prior to providing the connection parameters to the receiving device, the method further comprises: determining availability of a receiving device to receive the ultrasound image feed, the determining being performed using a second communications protocol different from the first communications protocol, wherein the providing the connection parameters is performed over the second communications protocol. In some embodiments, the first communications protocol comprises a Wi-Fi™ protocol, and the second communications protocol comprises a Bluetooth™ protocol.

In some embodiments, the first link-layer connection is formed using a first communications protocol, and prior to providing the connection parameters to the receiving device, the method further comprises: advertising availability of the multi-use display device to provide the connection parameters, the advertising being performed using a second communications protocol different from the first communications protocol, wherein the providing the connection parameters is performed over the second communications protocol. In some embodiments, the first communications protocol comprises a Wi-Fi™ protocol, and the second communications protocol comprises a Bluetooth™ protocol.

In another broad aspect of the present disclosure, there is provided a method of providing viewing access to an ultrasound image feed generated at an ultrasound imaging machine, the method comprising, at the ultrasound imaging machine: forming a first link-layer connection with a multi-use display device, the first link-layer connection being for receiving commands that control imaging parameters of the ultrasound image feed, wherein the multi-use display device: determines link-layer connection parameters that allow the ultrasound imaging machine to form a second link-layer connection with a receiving device, the receiving device having no link-layer connection with the ultrasound imaging machine, and provides the connection parameters to the receiving device; based on the connection parameters, receiving a request from the receiving device to form the second link-layer connection; forming the second link-layer connection with the receiving device; and providing viewing access of the ultrasound image feed to the receiving device using the second link-layer connection.

In some embodiments, the first link-layer connection and the second link-layer connection are each formed using a wireless local area network (WLAN) connection. In some embodiments, the connection parameters comprise: a service set identifier (SSID) associated with the WLAN, and a password for connecting to the WLAN.

In some embodiments, the receiving device comprises a dongle having a port for connecting an image output device, wherein one or more ultrasound images from the ultrasound image feed received at the receiving device is provided to the image output device via the port. In some embodiments, the commands that control imaging parameters of the ultrasound image feed comprise a signal marking the one or more ultrasound images from the ultrasound image feed to be provided to the image output device via the port, and the signal is transmitted from the ultrasound imaging machine to the receiving device.

In some embodiments, the first link-layer connection is formed using a first communications protocol, and prior to providing the connection parameters to the receiving device, the multi-use display device: advertises availability of the multi-use display device to provide the connection parameters to the receiving device, the advertising being performed using a second communications protocol different from the first communications protocol, wherein the providing the connection parameters is performed over the second communications protocol. In some embodiments, the first communications protocol comprises a Wi-Fi™ protocol, and the second communications protocol comprises a Bluetooth™ protocol.

In another broad aspect of the present disclosure, there is provided a method of providing viewing access to an ultrasound image feed generated at an ultrasound imaging machine, the method comprising, at the ultrasound imaging machine: forming a first link-layer connection with a multi-use display device, the first link-layer connection being for receiving commands that control imaging parameters of the ultrasound image feed, wherein the first link-layer connection is formed using a first communications protocol; advertising availability of viewing access to the ultrasound image feed, the advertising being performed using a second communications protocol different from the first communications protocol, wherein the advertising includes connection parameters that allow the ultrasound imaging machine to form a second link-layer connection with a receiving device using the first communications protocol; based on the connection parameters, receiving a request from the receiving device to form the second link-layer connection, the request being received using the first communications protocol; forming the second link-layer connection with the receiving device; and providing viewing access of the ultrasound image feed to the receiving device using the second link-layer connection.

In another broad aspect of the present disclosure, there is provided a method of obtaining viewing access to an ultrasound image feed generated at an ultrasound imaging machine, the method comprising, at a receiving device: determining link-layer connection parameters from one of: the ultrasound imaging machine and a multi-use display device, wherein the ultrasound imaging machine has a first link-layer connection with the multi-use display device, and the first link-layer connection is for the multi-use display device to transmit commands to the ultrasound imaging machine to control imaging parameters of the ultrasound image feed; based on the connection parameters, sending a request to the ultrasound imaging machine for the ultrasound imaging machine to form a second link-layer connection with the receiving device; forming the second link-layer connection with the ultrasound imaging machine; and receiving, via the second link-layer connection, the ultrasound image feed generated at the ultrasound imaging machine.

In some embodiments, the receiving device comprises another multi-use display device, and the method further comprises displaying the ultrasound image feed at the receiving device.

In some embodiments, the receiving device comprises a dongle having a port for connecting an image output device, and wherein the method further comprises: providing one or more ultrasound images from the ultrasound image feed received at the receiving device to the image output device via the port.

In some embodiments, the image output device comprises a simple display. In some embodiments, the image output device comprises an ultrasound image printer.

In some embodiments, the commands that control imaging parameters of the ultrasound image feed comprise a signal marking the one or more ultrasound images from the ultrasound image feed to be provided to the image output device via the port, and prior to providing the one or more ultrasound images to the image output device, the method further comprises: receiving the signal from the ultrasound imaging machine; and based on the signal, marking the one or more ultrasound images for providing to the image output device via the port.

In some embodiments, prior to providing the one or more ultrasound images to the image output device, the method further comprises: receiving a signal from the multi-use display device, the signal marking the one or more ultrasound images from the ultrasound image feed to be provided to the image output device via the port; and based on the signal, marking the one or more ultrasound images for providing to the image output device via the port.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is a functional block diagram of an ultrasound system, according to at least one embodiment of the present disclosure. Ultrasound imaging system 100 may include a multi-use display device 102, an ultrasound imaging machine 104, and a receiving device 106. For ease of reference, the ultrasound imaging machine 104 may also be referred to herein simply as an "ultrasound machine". Likewise, the multi-use display device 102 may also be referred to herein as the "display device". In various instances, the multi-use display device 102 may also be referred to herein as the "controlling device" because aspects of the ultrasound image feed may be controlled thereon.

The multi-use display device 102 may include a processor 120, memory 124, user interface 126, and an external interface 122. Processor 120 may be a central processing unit (CPU) or may be a low power/mobile specific processor. Processor 120 may be coupled with memory 124. Memory 124 may include storage for program and program operating code. One or more programs or applications (e.g., "apps") 124A in memory 124 may coordinate interactions of multi-use display device 102 with ultrasound imaging machine 104 and/or receiving device 106. In some embodiments, the multi-use display device 102 may be a tablet computer or a mobile device running iOS™, Android™ or other suitable operating system.

User interface 126 may be coupled with processor 120 and may include both the software and hardware components necessary to interface with a user of the multi-use display device 102. User interface 120 may include physical input components such as a touch-sensitive display screen, keyboard, microphone, or function buttons. User interface 120 may further include output devices such as a color, grayscale, or black and white display screen, audio speaker/output, vibrating and/or light-emitting diode (LED) indicators.

External interface 122 may be coupled with processor 120 and may provide connectivity of multi-use display device 102 with ultrasound imaging machine 104 through communication link 108A. External interface 122 may also be operable to communicate with another device, such as a web server and/or receiving device 106 (e.g., via communication link 108C), for example.

Processor 120 may generate control commands to control an operation of ultrasound imaging machine 104 according to information that is provided via user interface 126. The commands may control ultrasound imaging machine 104 to generate ultrasound signals, and/or control how the ultrasound imaging machine 104 handles transmission and reception of the ultrasound signal for generating an ultrasound image feed. For example, commands may be inputted via the user interface 126 at the multi-use display device 102 to control imaging parameters of the ultrasound image feed being generated at the ultrasound imaging machine 104. Based on the imaging parameters, the ultrasound imaging machine 104 may transmit ultrasound signals to a target object and receive echoes in response to generate an ultrasound image in the ultrasound image feed. Imaging parameters include factors that affect how ultrasound signals are transmitted and received. For example, these may include the ultrasound sequence, focus of ultrasound signals, imaging depth, and/or frequency of the ultrasound signals.

Throughout the description herein, a "target object" may be a target inanimate object or a target animate object, which is displayed via an image. Also, the target object may be a part of a human body and may include the liver, the heart, the womb, the brain, the breast, the abdominal region, or the like, a fetus, or a cross-section of a part of the human body. Throughout the following description, a "user" may be a medical expert including a doctor, a nurse, a medical laboratory technologist, a sonographer, or the like.

Additionally or alternatively, processor 120 may control wireless communication with ultrasound imaging machine 104, and may control generation and display of an ultrasound image on a display of user interface 126 based on ultrasound image data provided from ultrasound imaging machine 104. As discussed below, processor 120 may also control wireless communication with receiving device 106.

Still referring to FIG. 1, ultrasound imaging machine 104 may include a processor 140, memory 144, imaging unit 146, pairing unit 148, and a communication unit 142. Processor 140 may include a CPU, a low power/mobile specific processor, a field programmable gate array, a combination of two or more of these or the like.

Imaging unit 146 may be operable to acquire ultrasound image data of a target object based on control signals from processor 140. Imaging unit 146 may include a transmitter for generating ultrasound energy, and a receiver for receiving ultrasound energy reflected from the target object. Imaging unit 146 may include an analog-to-digital converter (ADC) for digitizing the received ultrasound energy into digital ultrasound data. Imaging unit 146 may also include one or more beamformers to combine and focus the received ultrasound energy along a desired scanline. Imaging unit 146 may further include a signal processor to apply filtering or compression to the ultrasound image data.

In various embodiments, imaging unit 146 may include a scan converter for converting the ultrasound image data into a specific display format. However, in some embodiments, a scan converter may not be provided at the ultrasound imaging machine 104. Instead, a scan converter (or appropriate software instructions for performing scan conversion) may be provided at the multi-use display device 102 and/or the receiving device 106. As discussed below with respect to FIG. 10, the multi-use display device 102 and a given receiving device 106 may have different configurations (e.g., a display device 102 may be a tablet computer, whereas a receiving device 106 may be a smartphone or a television display). Performing scan conversion at the destination device instead of at the ultrasound imaging machine 104 may allow for adapting of an ultrasound image feed to the display format of the destination device (e.g., adapting for different aspect ratios and/or resolutions of the different displays).

Referring still to FIG. 1, processor 140 may be coupled with memory 144. Memory 144 may include storage for software 144A (e.g., program and/or program operating code). One or more programs in memory 144 may coordinate the operation of ultrasound imaging machine 104 as described herein. Memory 144 may also be used to store information about ultrasound imaging machine 104 and/or ultrasound image data.

Pairing unit 148 may be operable to establish communication link 108A between communication unit 142 and external interface 122 of multi-use display device 102. Communication unit 142 may include one or more wireless transceivers. As discussed below, the pairing unit 148 may also be operable to establish communication link 108B between the communication unit 142 and the external interface 162 of the receiving device 106, to provide access to the ultrasound image feed being controlled by the multi-use display device 102.

Ultrasound imaging machine 104 may have any of a wide range of various sizes and configurations. For example, ultrasound imaging machine 104 may be handheld or hand carried. Alternatively, ultrasound imaging machine 104 may be in a laptop form factor or a more traditional cart-based form factor. In some embodiments, ultrasound imaging machine 104 may have the form of hand-held, battery-powered probes. In an example embodiment, the ultrasound imaging machine 104 may be provided in the form of a portable handheld ultrasound scanner that can communicate wirelessly to a multi-use display device 102 and/or one or more receiving devices 106.

Referring still to FIG. 1, receiving device 106 may include a processor 160, memory 164, and an external interface 162. Processor 160 may be a central processing unit (CPU) or may be a low power/mobile specific processor. Processor 160 may be coupled with memory 164. Memory 164 may include storage for firmware and/or software 164A (e.g., program and program operating code), depending on the configuration of the receiving device 106. The firmware/software 164A in memory 164 may coordinate interactions of receiving device 106 with ultrasound imaging machine 104 and/or the controlling device 102.

Receiving devices 106 may take different forms in various embodiments. Depending on the configuration, a receiving device 106 may have one or more output components. For example, a receiving device 106 may include a display 166 and/or a port 168. These elements are optional and may not necessarily be included with all receiving devices 106. As such, they are shown in dotted outline in FIG. 1. In an example scenario, the receiving device 106 may be a dongle having a port 168 for connecting an image output device such as a simple display (e.g., a larger external television) or an ultrasound image printer.

In another example scenario, where the receiving device 106 includes a display 166, the receiving device 106 may be similar to the multi-use display device 102. In such case, software 164A executing on the receiving device 106 may be substantially similar to software 124A executing on the display device 102. For example, the same application (e.g., downloadable from an application store available on a mobile device operating system such as iOS™ or Android™) may execute on both the display device 102 and the receiving device 106, and the application can be configurable to operate in both a regular mode on the display device 102 to control operation of the ultrasound imaging machine 104, and a viewing mode on the receiving device 106 for receiving view-only access to an ultrasound image feed generated by the ultrasound imaging machine 104.

External interface 162 of receiving device 106 may be coupled with processor 160, and may provide connectivity of the receiving device 106 to the ultrasound imaging machine 104 through communication link 108B. The receiving device 106 may receive the ultrasound image feed through external interface 162. External interface 162 may also be operable to communicate with another device, such as a web server or display device 102 (e.g., through communication link 108C), for example.

The display 166 and/or the port 168 may be coupled with processor 160 so that one or more images of the ultrasound image feed may be outputted thereto. In various embodiments, the receiving device 106 may also include a user interface (not shown on receiving device 106 in FIG. 1) similar to user interface 126 of multi-use display device 102 described above. This user interface may be a part of, or separate from, the display 166.

Input may be provided via a user interface on receiving device 106 to cause the processor 160 to receive connection parameters to form the communication link 108B with the ultrasound imaging machine 104. This communication link 108B may allow the receiving device 106 to receive the ultrasound image feed being generated at the ultrasound imaging machine 104 (and controlled at the multi-use display device 102). The processor 160 may process the ultrasound image feed to, for example, output the ultrasound image feed for display on the display 166 and/or output one or more images from the ultrasound image feed to an image output device via port 168.

In various embodiments, the ultrasound image feed being provided to the receiving device 106 may be similar to the one provided to the multi-use display device 102. For example, the ultrasound image feed transmitted from the ultrasound imaging machine 104 may be in pre-scan-converted format (e.g., polar coordinates), so that scan conversion is performed by processor 120 and processor 160 on the multi-use display device 102 and the receiving device 106 respectively (e.g., scan converted to be in cartesian coordinates suitable for each respective device). Configuring the ultrasound image feed transmitted from the ultrasound imaging machine 104 to be in pre-scan converted format may allow such format to be the same regardless of the destination device (e.g., the same format can be used whether it is transmitted to the multi-use display device 102 or the receiving device 106). This may allow the ultrasound imaging machine 104 to reuse the same software code 144A that transmits the ultrasound image feed to the multi-use display device 102 when transmission is being made to the receiving device 106. This may reduce complexity of the software code 144A at the ultrasound imaging machine 104. Also, as noted, performing scan conversion at the destination device may allow the same ultrasound image feed to be adapted to various display formats of either the display device 120 and/or multiple receiving devices 106.

Referring still to FIG. 1, it can be noted that ultrasound imaging machine 104 may establish multiple communication links with external devices. As shown, the ultrasound imaging machine 104 may establish a first communication link 108A with multi-use display device 102. This communication link 108A may allow the multi-use display device 102 to transmit commands to the ultrasound imaging machine 104, and the ultrasound imaging machine 104 to transmit an ultrasound image feed from the ultrasound imaging machine 104 to the multi-use display device 102. A second communication link 108B may allow the ultrasound imaging machine 104 to provide view-only access of an ultrasound image feed to one or more receiving devices 106.

In various embodiments, the communication unit 142 of ultrasound imaging machine 104 may include suitable hardware to communicate using more than one communications protocol. Corresponding external interfaces 122, 162 on multi-use display device 102 and/or receiving device 106 respectively may also be configured to communicate using more than one communications protocol so that communications may take place over communication links 108A, 108B using multiple communications protocols.

For example, in cases of wireless transmission of an ultrasound image feed, a high-bandwidth connection such as Wi-Fi™ may be desired. While some communications protocols (e.g., Bluetooth™) may allow for ease of discoverability, these protocols typically have a lower bandwidth that may not be sufficient to transmit a high-quality ultrasound image feed (e.g., Bluetooth™ bandwidth may not exceed one (1) megabyte per second). In some embodiments, the primary link between an ultrasound imaging machine 104 and a multi-use display device 102 may be achieved using a communications protocol (e.g., Wi-Fi™) that has sufficient bandwidth to allow the transmission of the ultrasound image feed from the ultrasound imaging machine 104 to the multi-use display device 102.

To allow the receiving device 106 to receive the ultrasound image feed, the receiving device 106 may also need to form a communication link with the ultrasound imaging machine 104 using an analogous communications protocol that has sufficient bandwidth. However, the steps for the receiving device 106 to discover and establish a connection with an ultrasound machine 104 using the higher-bandwidth communications protocol may not be as straightforward as using the narrower-bandwidth protocol.

For example, in the case where the higher-bandwidth communications protocol is Wi-Fi™ and the receiving device 106 had no previous Wi-Fi™ connection with the ultrasound imaging machine 104, a user may be required to interact with the settings menu of a receiving device 106 to select a Service Set Identifier (SSID) of the Wireless Local Area Network (WLAN) being broadcasted by the ultrasound machine 104. Then, a user may need to type in a password to join the WLAN. This may cause inconvenience for a user.

As will be understood by persons skilled in the art, the bandwidth of a communications protocol may typically be a characteristic of the physical and data link layers of the Open Systems Interconnection (OSI) model for organizing functions of data communications. For example, WLAN connections may operate at the physical and link-layers of the OSI model. The present embodiments generally relate to methods of providing link-layer connection parameters (e.g., an SSID and associated password) to a receiving device 106 to facilitate ease of establishing the link-layer connection between the receiving device 106 and the ultrasound machine 104.

Unlike screen-mirroring techniques between devices that can discover each other if they are already connected via data and data link-layer connections, the establishment of a link-layer connection at lower levels of the OSI model may require the receiving device 106 to be in possession of the link-layer connection parameters. The present embodiments facilitate providing the connection parameters to the receiving device 106. Notably, in situations where a WLAN communications protocol is used to form the communications link 108A between the display device 102 and the ultrasound machine 104, the display device 102 may not be able to use many existing screen mirroring technologies because the display device 102 may be only able to form a single Wi-Fi™ connection, and that connection is needed to be formed with the ultrasound machine 104. Thus, the display device 102 may not be able to join another local WLAN hotspot to take advantage of existing screen mirroring technologies. Furthermore, screen mirroring technologies may not be a good solution for providing an ultrasound image feed from the display device 102 to the receiving device 106 because even though a higher bandwidth communications protocol is being used, the protocol may not have sufficient bandwidth to allow the display device 102 to both receive the ultrasound image data for display, and further forward such data to the receiving device 106.

Several example communication protocols such as Bluetooth™ and Wi-Fi™ have been discussed above. However, other types of communications protocol may also be used with the methods described herein. For example, other communications that may be used include: a Bluetooth™ low energy (BLE) connection, ZigBee™, Wi-Fi Direct (WFD), ultra wideband (UWB), infrared data association (IrDA), near field communication (NFC), wireless broadband internet (Wibro), world interoperability for microwave access (WiMAX), shared wireless access protocol (SWAP), radio frequency (RF) communications, radio frequency identification (RFID), and the like.

The embodiments described herein generally allow the receiving device 106 to establish a second communications link 108B with the ultrasound imaging machine 104 for receiving the ultrasound image feed being controlled by, and transmitted to, the multi-use display device 102. As described herein, the connection parameters for establishing the second communications link 108B may be provided from the multi-use display device 102 to the receiving device 106 so that the receiving device 106 may directly establish the second communications link 108B with the ultrasound imaging machine 104.

Figure 2:
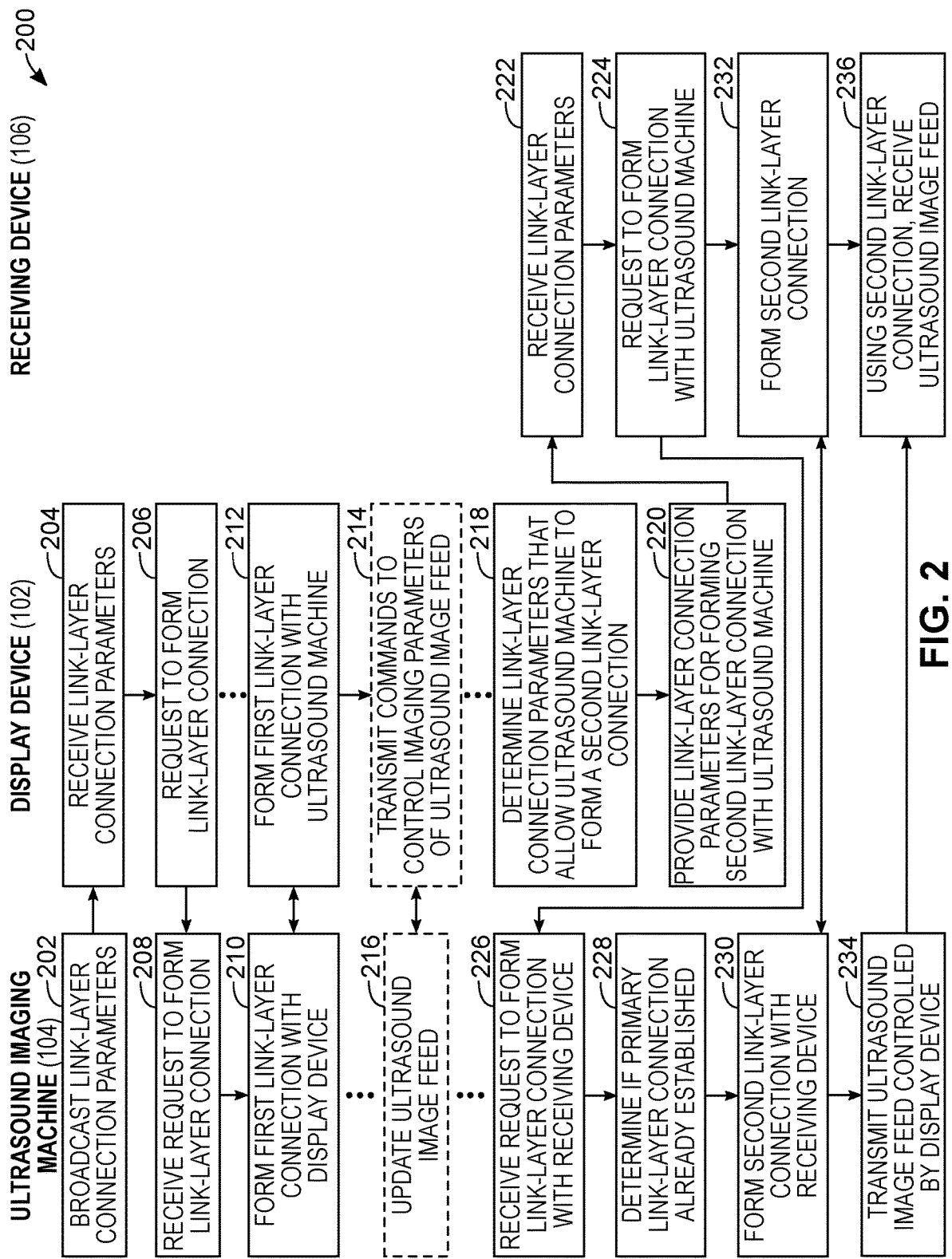
FIG. 2 shows a flowchart diagram with acts of establishing a secondary connection at an ultrasound imaging machine for providing access to an ultrasound image feed, according to at least one embodiment of the present disclosure.

Referring to FIG. 2, shown there generally as 200 is a flowchart diagram with acts of establishing a secondary connection at an ultrasound imaging machine for providing access to an ultrasound image feed, according to at least one embodiment of the present disclosure. The method of FIG. 2 shows interaction amongst the ultrasound imaging machine 104, the multi-use display device 102, and the receiving device 106 shown in FIG. 1. In describing the method shown in FIG. 2, reference may also be made to the example user interfaces shown in FIGS. 3 and 4.

At 202, the ultrasound imaging machine 104 may broadcast link-layer connection parameters. For example, the link-layer connection may be a Wi-Fi™ connection that allows for formation of a Wireless Local Area Network (WLAN) amongst the ultrasound imaging machine 104, the multi-use display device 102, and/or the receiving device 106. The connection parameters may include a service set identifier (SSID) associated with the WLAN, and a password for connecting to the WLAN. At 204, the display device 102 may receive the link-layer connection parameters from the ultrasound imaging machine 104.

At 206, the display device 102 may request to form the link-layer connection with the ultrasound machine 104 using the connection parameters received at act 204. In various embodiments, the display device 102 may display the connection parameters, and initiation of the request to form the link-layer connection may result from receipt of user input at the display device 102. In some embodiments, the display device 102 may automatically request to form the link-layer connection 102 based on connection parameters received at act 204. For example, in scenarios where the link-layer connection is a Wi-Fi™ connection, the automatically forming of the connection may be implemented by accessing a Wi-Fi™ auto-join application programming interface (API) available on the operating system of the display device 102.

At 208, the ultrasound imaging machine 104 may receive the request to form a link-layer connection with the display device 120. At acts 210-212, based on the request received at act 208, the ultrasound imaging machine 104 may form a first link-layer connection with a multi-use display device 102. This first-link layer connection may allow the ultrasound imaging machine 104 to receive commands that control imaging parameters of the ultrasound image feed being generated. For example, these imaging parameters may include imaging depth, focus, and/or anatomy pre-sets. Communications for transmitting commands and the updating of the ultrasound image feed may occur at acts 214-216. These acts are shown in dotted outline to indicate they are optional, as acts 214-216 may not necessarily be performed prior to acts 218-236.

At 218, the display device 102 may determine link-layer connection parameters that allow the ultrasound imaging machine 104 to form a second link-layer connection 108B (as shown in FIG. 1) with a receiving device 106. As noted, in example embodiments where the link-layer connection is a Wi-Fi™ connection, these connection parameters may include a SSID and a password for joining the WLAN identified by the SSID. Additionally or alternatively, the connection parameters may include network-layer parameters such as an Internet Protocol (IP) address and port number. After a link-layer connection has been established, the network-layer parameters may be used by software executing on the receiving device 106 to also form a network-layer connection to the ultrasound imaging machine 104 that allows the receiving device 106 to receive and process the ultrasound image feed.

Notably, the receiving device 106 may have no previous link-layer connection with the ultrasound imaging machine 104 such that the connection parameters for establishing the second link-layer connection 108B would not be cached or otherwise available at the receiving device 106. For example, this may occur in an educational setting where students may use their own receiving devices 106 to receive an ultrasound image feed from an ultrasound imaging machine 104 being operated by an instructor.

Another scenario where the present embodiments may be desirable is when the ultrasound imaging machine 104 is provided in an ultraportable form (e.g., in the form of a wireless handheld scanner that connects to an external display device 102 for receiving commands and displaying an ultrasound image feed). The ultraportable characteristics of an ultrasound imaging machine 104 may allow it to be more easily transported to multiple locations (e.g., it may accompany a physician or other ultrasound operator to multiple hospitals or clinics) such that ultrasound imaging machine 104 may frequently connect to new receiving devices 106 at those varying locations.

In a further scenario, the ultrasound imaging machine 104 may be used in a clinic, and new patients may frequently connect their own receiving device 106 to the ultrasound machine 104 being used at a clinic to view the ultrasound images being taken. For example, this may be desirable in obstetrics/gynecology specialties where an expecting mother may desire to hold a receiving device 106 in their hands during an examination to more easily view ultrasound images being obtained of a fetus. As new patients come into the clinic, they may use their own mobile devices as receiving devices 106 in this manner. This may result in many receiving devices 106 with no previous link-layer connection frequently attempting to form new connections with an ultrasound imaging machine 104 being used at the clinic, such that the ease of providing connection parameters in the manner described herein may be particularly desirable.

Referring still to FIG. 2, at 220, the display device 120 may provide the connection parameters to the receiving device 106. This may be performed in various ways. In some embodiments, the connection parameters may be provided via an optical communication channel. For example, this may involve the display device 120 displaying a barcode embedding the connection parameters so that the barcode can be read by a barcode reader on the receiving device 106.

Figure 3:
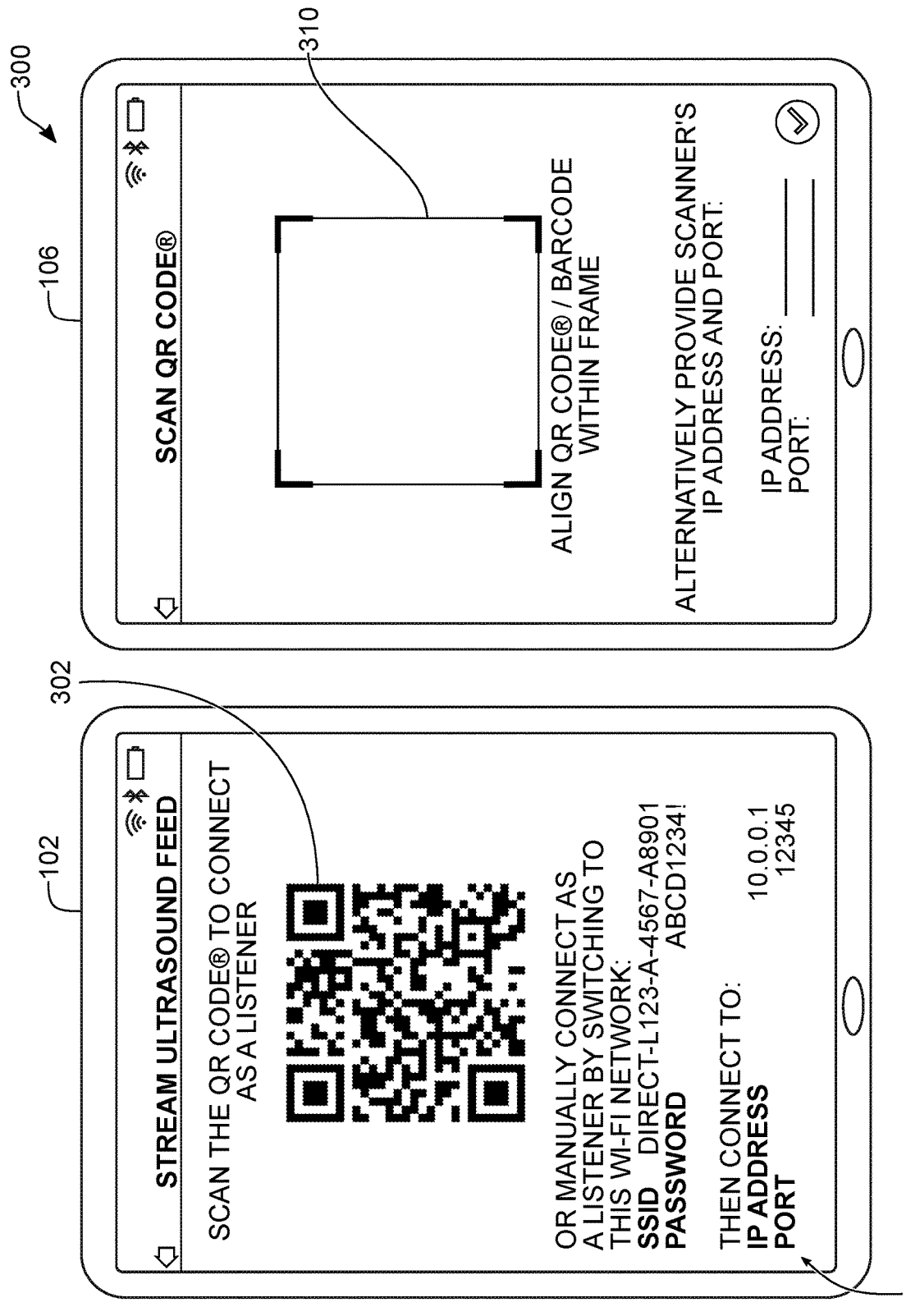
FIGS. 3 and 4 show example user interfaces on a multi-use display device and a receiving device that allow the receiving device to establish a secondary connection with an ultrasound machine that is already connected to the multi-use display device, according to at least one embodiment of the present disclosure.

Referring simultaneously to FIG. 3, shown there generally as 300 are example user interfaces on a multi-use display device 102 and a receiving device 106 that allow the receiving device 106 to establish a secondary connection with an ultrasound machine 104 connected to the multi-use display device 102, according to at least one embodiment of the present disclosure. As noted above, in some example embodiments, a single downloadable ultrasound application may be operable in multiple modes: a regular mode that establishes a primary connection with an ultrasound imaging machine 104 to control imaging parameters, and a view-only mode that establishes a secondary connection with the ultrasound imaging machine 104 for simply receiving (but not controlling) the ultrasound image feed. Depending on the mode the application is executing, a given mobile computing device may considered either a display device 102 or a receiving device 106 as described herein. Alternatively, dedicated separate applications may be provided for controlling imaging parameters and obtaining view-only access.

As shown in FIG. 3, the display device 102 may be operating in the regular mode, and is configured to display a two-dimensional Quick Response (QR) code 302 that embeds the connection parameters. As shown, a QR code is shown; however, in various embodiments, other types of barcodes may also be used. In the user interface shown in the display device 102, the term "Listener" is also used to refer to the receiving device 106.

The receiving device 106 may have a camera or other optical sensor that allows it to read the barcode 302 being displayed at the display device 102. In the example illustrated in FIG. 3, a software application executing on the receiving device 106 may be operating in a view-only mode that accesses a camera available on the receiving device 106 to configure it to be used as a barcode reader. For example, the user interface on the receiving device 106 may overlay the images from the camera with a barcode reader that requests for alignment of a displayed barcode 302 within a frame 310. Once the barcode 302 is read at the receiving device 106, the connection parameters may be determined by the receiving device 106. In an example embodiment, the receiving device 106 may provide the barcode reader by implementing a barcode scanning library such as the "ZXing" ("Zebra Crossing") library.

In FIG. 3, the display device 102 also shows instructions 304 for manually establishing a second link-layer connection with the ultrasound imaging machine 104 (e.g., the SSID and password for establishing a Wi-Fi™ connection with the ultrasound imaging machine 104). Instead of scanning the barcode using the user interface shown in FIG. 3, a user of the receiving device 106 may use these instructions to manually identify the SSID in the Wi-Fi™ settings of a receiving device 106 and connect to the ultrasound imaging machine 104 using the password indicated. However, manual connection is cumbersome, and providing the connection parameters via the barcode may increase ease of use.

Also shown in FIG. 3 are the transport-layer parameters such as an IP address and port number. In various embodiments, these parameters may also be embedded in the barcode 302 to allow the receiving device 106 to form a transport-layer connection with the ultrasound imaging machine 104. In FIG. 3, the user interface on the receiving device 106 also provides user interface text fields that allow for manual entry of the IP address and port number if the link-layer connection was being established manually.

The embodiment shown in FIG. 3 is configured to allow for unicast transmission between the ultrasound imaging machine 104 and a receiving device 106, such that the receiving device 106 may need information about the IP address and port number of the ultrasound machine 104. However, additionally or alternatively, the ultrasound machine 104 may be configured to use an IP multicast protocol for providing the ultrasound image feed to receiving devices 106. In such case, the receiving device 106 may be preconfigured with known IP multicast addresses, such that this information need not be provided to the receiving device 106.

Referring back to FIG. 2, another way of implementing act 220 is to provide the connection parameters to the receiving device 106 by communicating via a contactless communication channel. In some embodiments, the contactless communication channel may include a near field communication (NFC) communication channel. In this case, act 220 may involve configuring an NFC integrated circuit (IC) on the display device 102 to transmit the connection parameters for reading by a NFC reader on the receiving device 106.

Figure 4:
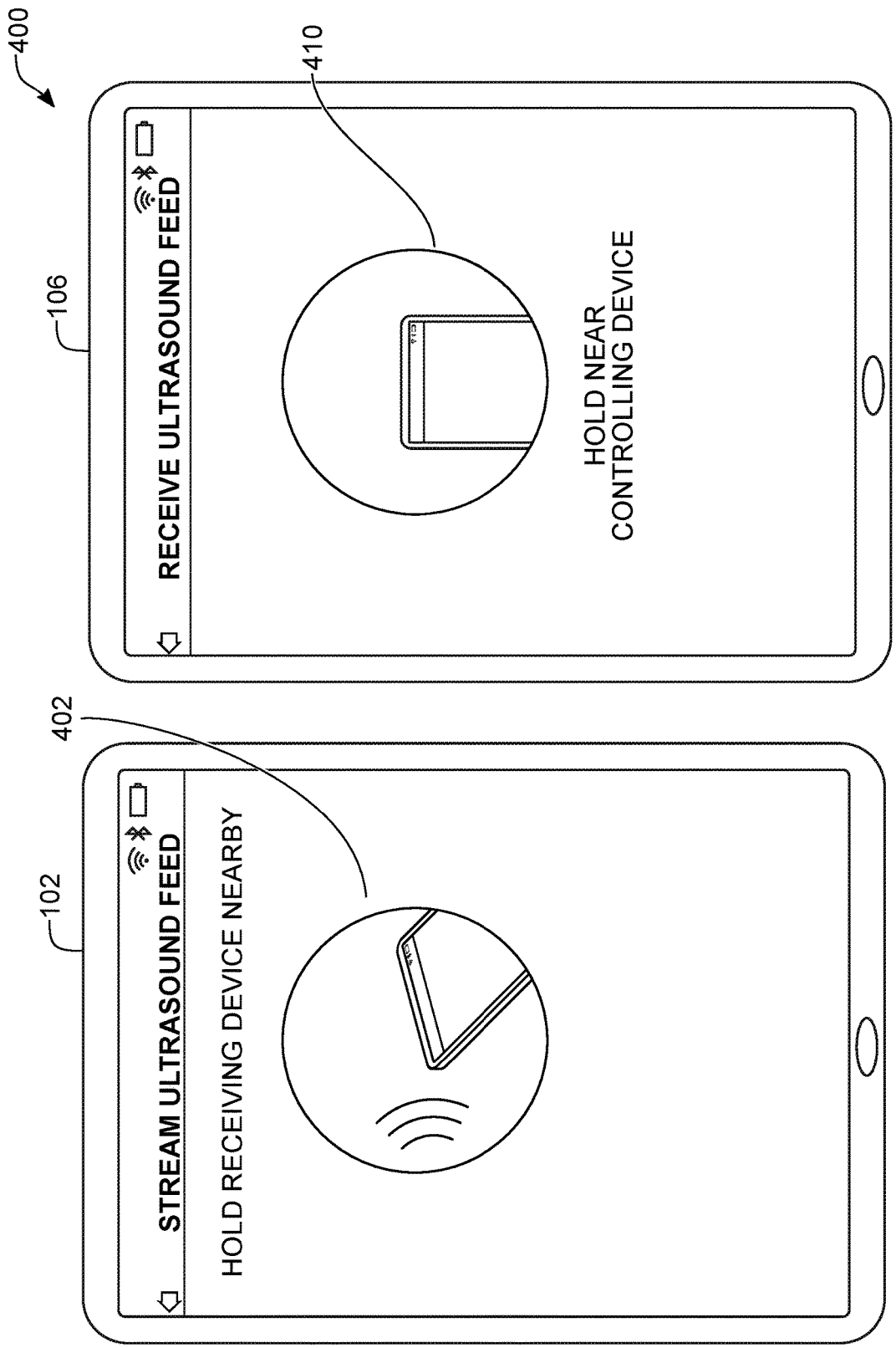

Referring simultaneously to FIG. 4, shown there generally as 400 are example user interfaces on a multi-use display device 102 and a receiving device 106 that allow the receiving device 106 to establish a secondary connection with an ultrasound machine 104 connected to the multi-use display device 102, according to at least one other embodiment of the present disclosure. As shown in FIG. 4, when the display device 102 is configuring the NFC IC to transmit the connection parameters in this manner, the user interface 126 (as shown in FIG. 1) may be configured to display a graphic 402 and associated text that informs a user to hold a receiving device 106 nearby to receive the connection parameters. When configured to be in a view-only mode for receiving an ultrasound image feed, the receiving device 106 may similarly show a graphic 410 to inform a user of the receiving device 106 to bring the receiving device 106 near the display device 102 so that it can activate its NFC reader to read the connection parameters from the display device 102. As compared to FIG. 3, the example user interfaces on the display device 102 and the receiving device 106 do not show the instructions 304 for manually establishing a second link-layer connection with the ultrasound imaging machine 104. Users may then be expected to use the NFC IC and reader to provide the connection parameters from the display device 102 to the receiving device 106.

Referring back to FIG. 2, at act 222, the receiving device 106 may receive the link-layer connection parameters. As discussed above, in some embodiments, this may be performed via the reading of barcode 302 (as shown in FIG. 3) or via an NFC reader (as shown in FIG. 4).

At act 224, based on the connection parameters, the receiving device 106 may send a request to the ultrasound imaging machine 104 for the ultrasound imaging machine 104 to form a second link-layer connection with the receiving device 106. This request may be received at the ultrasound imaging machine 104 (act 226).

At act 228, the ultrasound imaging machine 104 may determine if a primary (e.g., first) link-layer connection is already established. As illustrated, the ultrasound imaging machine 104 may determine that a first link-layer connection 108A (as shown in FIG. 1) has already been established with the display device 102. The method may then proceed to form the second link-layer connection 108B (as shown in FIG. 1) with the receiving device 106 (acts 230-232). However, if the ultrasound imaging machine 104 had determined that a primary link-layer connection was not already established, the ultrasound imaging machine 104 may determine that the connection request is for a primary link-layer connection 108A for controlling imaging parameters of the ultrasound image feed.

Acts 230-232 may involve a number of additional exchanges between the ultrasound imaging machine 104 and the receiving device 106 that are not shown in FIG. 2. In scenarios where the link-layer connection is a Wi-Fi™ connection, the receiving device 106 may automatically form the connection with the ultrasound machine 104 by accessing a Wi-Fi™ auto-join API available on the operating system of the display device 102.

At 234, the ultrasound imaging machine 104 may transmit the ultrasound image feed (as controlled by the display device 102) to the receiving device 106 using the second link layer connection 108B. In this way, the ultrasound imaging machine 104 may provide viewing access of the ultrasound image feed to the receiving device 106. The ultrasound image feed may be received at the receiving device 106 (act 236).

In various embodiments, the providing of the connection parameters to the receiving device 106 may be performed by the ultrasound imaging machine 104 itself. For example, in some embodiments, the ultrasound imaging machine 104 may be provided with suitable hardware components such as NFC or RFID integrated circuits that, when a receiving device 106 is brought within sufficient proximity, can provide the connection parameters to the receiving device 106.

As shown in FIG. 2, the connection parameters provided by the display device 102 to the receiving device at act 220 are for connecting to the ultrasound imaging machine 104 using the same communications protocol as the primary connection between display device 102 and the ultrasound imaging machine 104 (namely, a WLAN connection). This may allow the first link-layer connection and the second link-layer connection to each be formed using the same protocol technology (e.g., a wireless local area network (WLAN) connection). However, in other embodiments, the connection parameters may be for allowing the receiving device 106 to connect to the ultrasound imaging machine 104 using a communications protocol that is different from the communications protocol used in the first link-layer connection 108A (as shown in FIG. 1).

Figure 5:
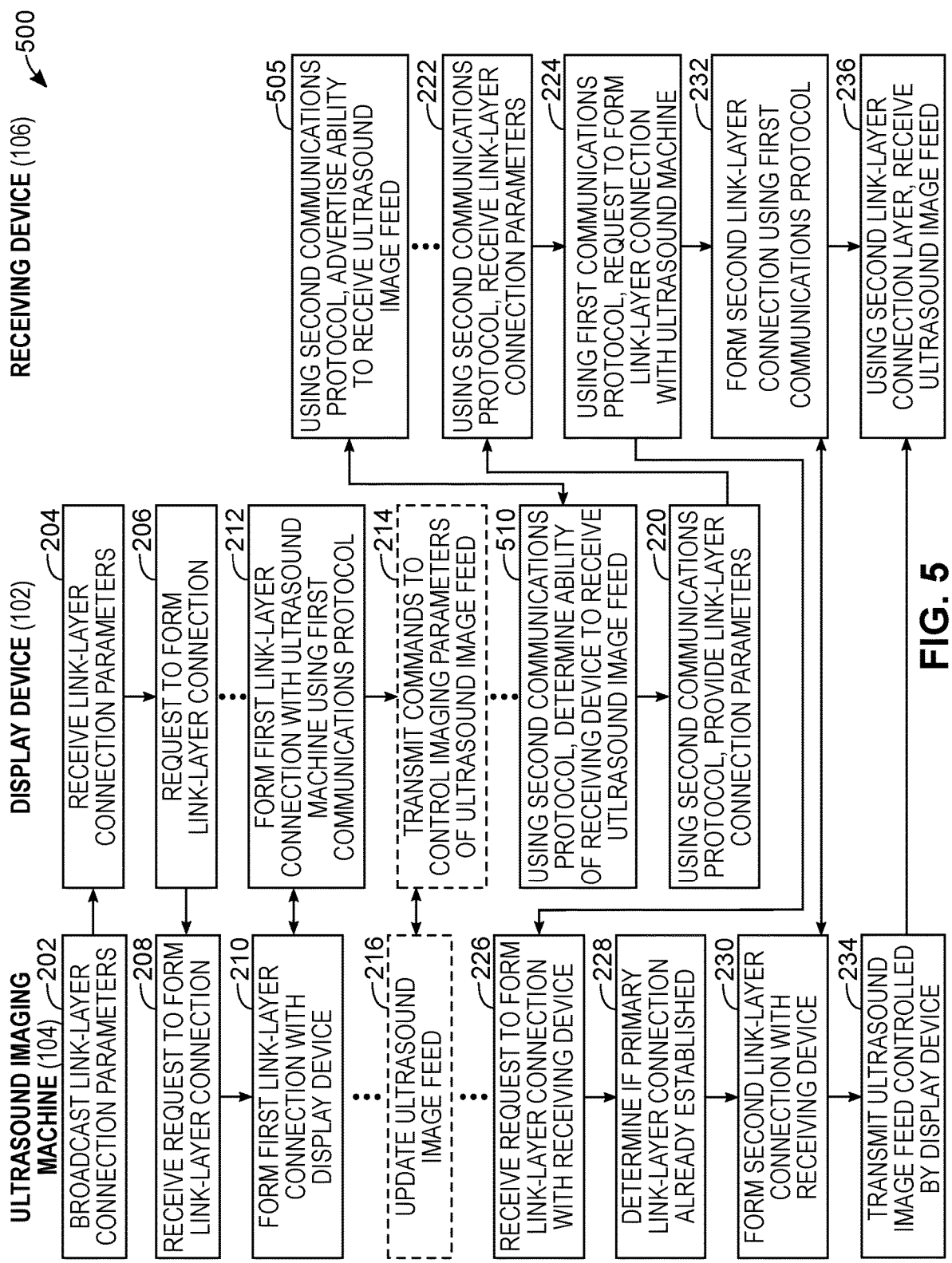
FIGS. 5, 7, and 9 show flowchart diagrams of acts for establishing a secondary connection at an ultrasound imaging machine by providing connection parameters over a second communications protocol, according to several embodiments of the present disclosure.
Figure 7:
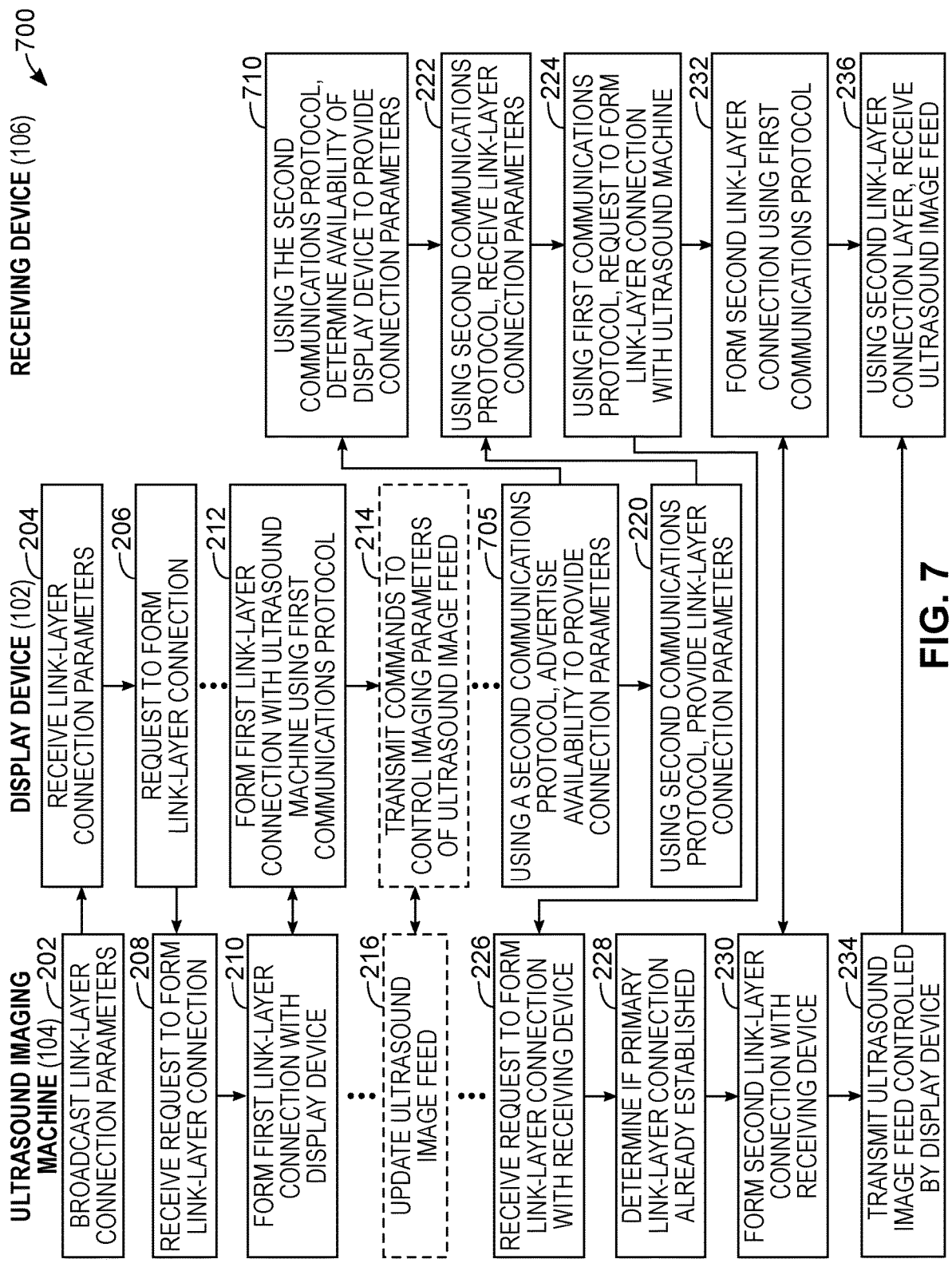
Figure 9:
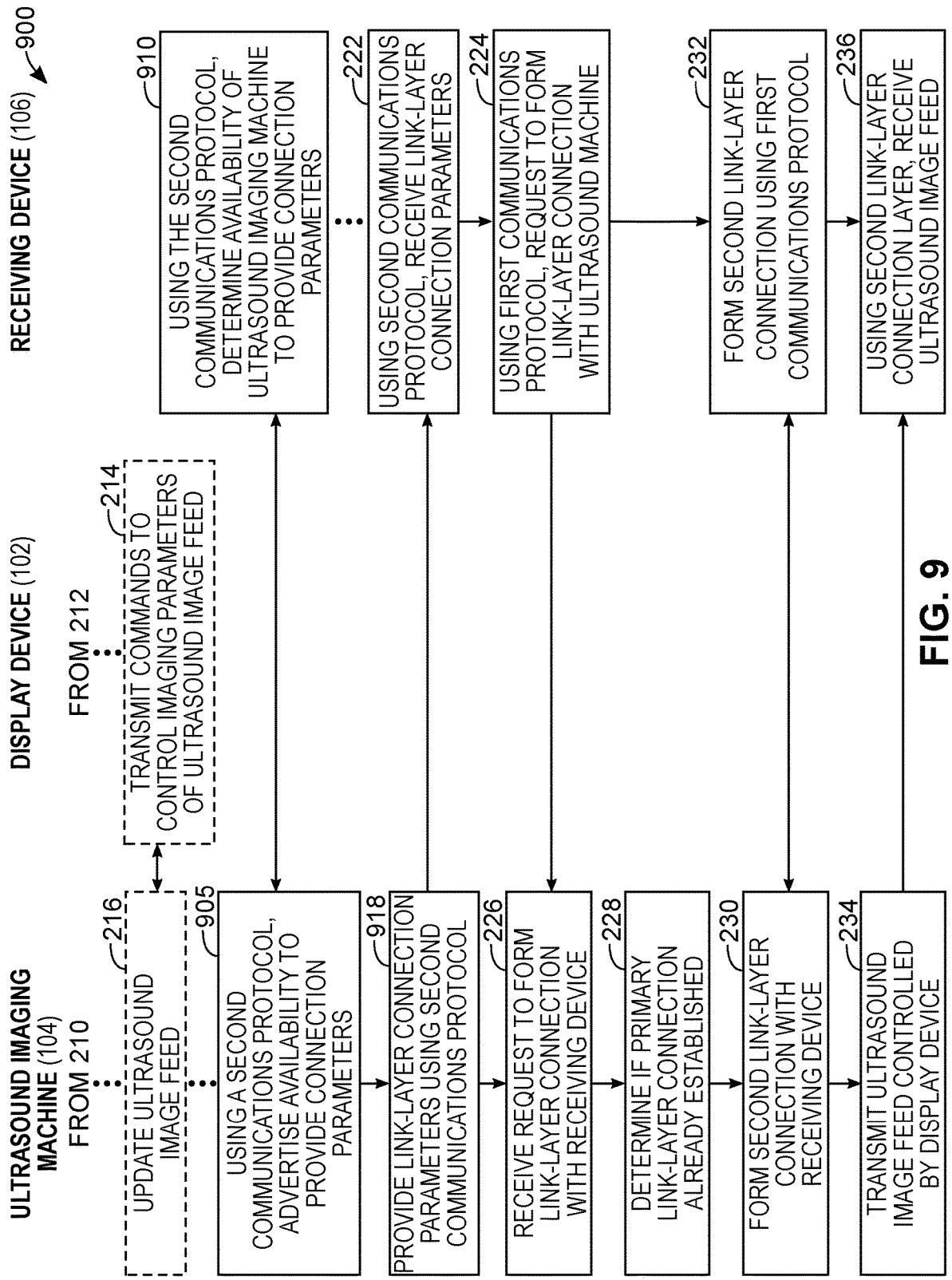

As discussed above, the ultrasound imaging machine 104 and/or the display device 102 may be provided with suitable hardware to communicate using multiple wireless communications protocols (e.g., Bluetooth™ and Wi-Fi™ radios). In some embodiments, the providing of connection parameters to the receiving device 106 may be performed using a second communications protocol (e.g., Bluetooth™) that is different from the first communications protocol (e.g., Wi-Fi™) used to establish the primary communication link 108A between the ultrasound imaging machine 104 and the display device 102. FIGS. 5, 7, and 9 show several example embodiments for how this may be performed. The methods shown in FIGS. 5 and 7 involve the display device 102 providing the connection parameters to the receiving device 106 via the secondary communications protocol. The method shown in FIG. 9 involves the ultrasound imaging machine 104 directly providing the connection parameters to the receiving device 106 via the secondary communications protocol.

Referring to FIG. 5, shown there generally as 500 is a flowchart diagram for acts of establishing a secondary connection at an ultrasound imaging machine 104 by providing connection parameters over a second communications protocol, according to at least one embodiment of the present disclosure. In FIG. 5, acts 202-216 may be performed in a similar manner to what was described above with respect to FIG. 2. While not shown in FIG. 5 for ease of illustration, an act analogous to act 218 for determining the link-layer connection parameters may also be performed in FIG. 5.

However, instead of act 220 providing the connection parameters via an optical communications channel (e.g., barcode) or a contactless communication channel (e.g., NFC), the connection parameters may be provided via a wireless communications link 108C (as shown in FIG. 1) formed using a second communications protocol different from the first communications protocol used to establish the first communications link 108A between the display device 102 and the ultrasound imaging machine 104.

To allow for the establishment of this second communications link 108C, at act 505, the receiving device 106 may, using the second communications protocol, advertise its ability to receive an ultrasound image feed. For example, in scenarios where the primary communications link 108A is established using a Wi-Fi™ connection, the second communications protocol may be a Bluetooth™ protocol and advertising may be performed using available communications packet configurations available for advertising in the Bluetooth™ protocol.

Figure 6:
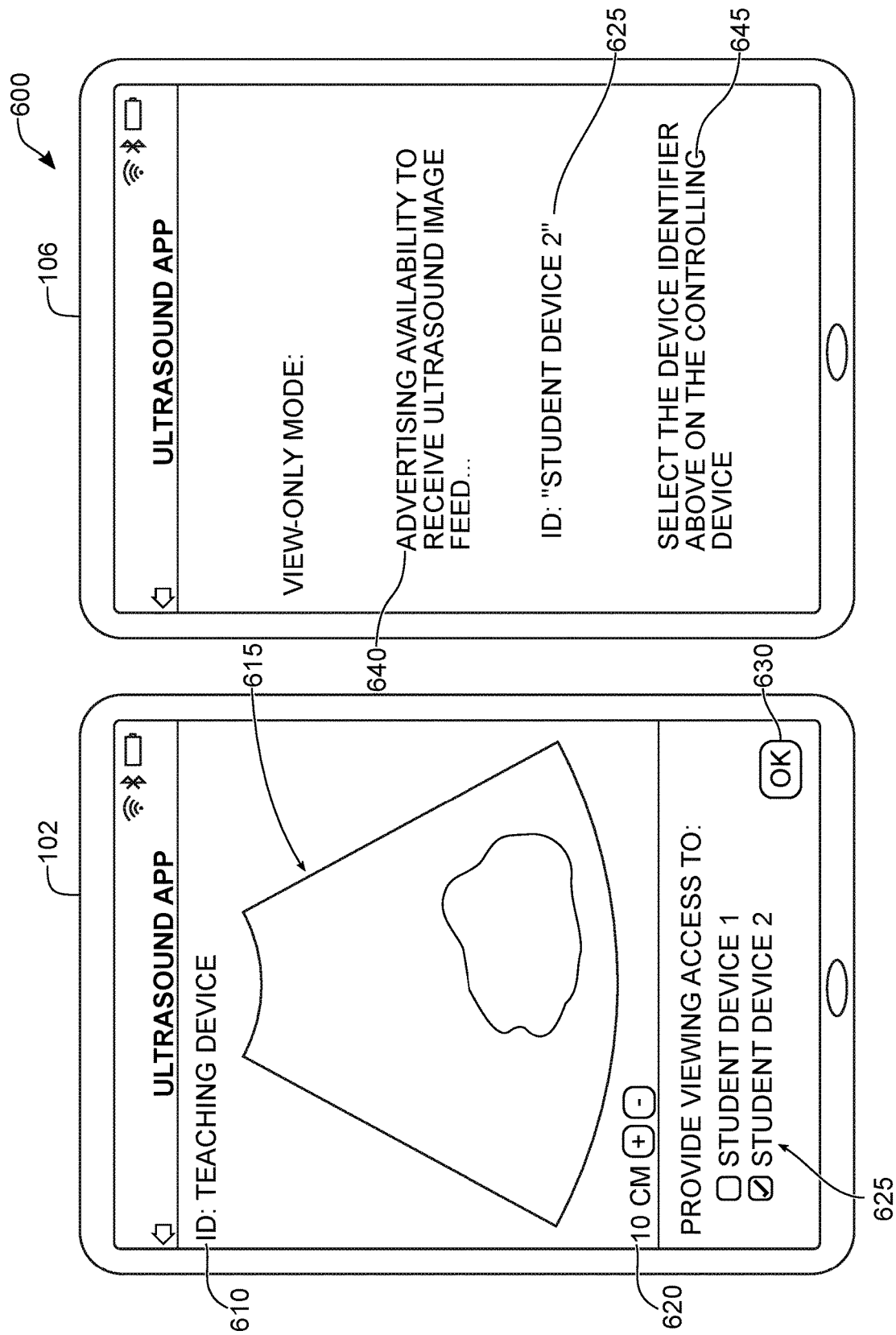
FIGS. 6 and 8 show example user interfaces on a multi-use display device and a receiving device that allow the receiving device to obtain connection parameters over a second communications protocol, according to several embodiments of the present disclosure.

Referring simultaneously to FIG. 6, shown there generally as 600 are example user interfaces on a multi-use display device 102 and a receiving device 106 that allow the receiving device 106 to obtain connection parameters over a second communications protocol, according to at least one embodiment of the present disclosure. As illustrated in FIG. 6, the receiving device 106 may be executing an ultrasound application that is being operated in a view-only mode. In this mode, the ultrasound application may be configured to advertise its ability to receive an ultrasound image feed, and in doing so, may display a user notification 640. When performing the advertising, the receiving device 106 may be configured to display device identifier 625 that allows it to be identified at the display device 102. A further notification 645 may be displayed to inform the user to select the device identifier 625 on the controlling display device 102.

Referring briefly back to FIG. 5, at 510, using the second communications protocol, the display device 102 may read the advertisement packets resulting from act 505 and determine the ability of the receiving device 106 to receive an ultrasound image feed.

Referring again also to FIG. 6, the display device 102 may be configured to display a user interface that shows an ultrasound image feed 615. In the illustrated example embodiment, the user interface may also include an imaging depth indicator 620, and an identifier 610 for the ultrasound imaging machine 104 the display device 102 is controlling (e.g., "Teaching Device"). In this example embodiment, the user interface of the display device 102 may be configured to provide a menu that allows for selection of a receiving device 106 to which the ultrasound image feed is to be transmitted.

The menu may be populated with receiving devices 106 that are advertising their availability to receive an ultrasound image feed (e.g., over a second communications protocol). For example, in FIG. 6, since the receiving device 106 may be advertising its availability to receive the ultrasound image feed, the device identifier 625 of the receiving device 106 (e.g., "Student Device 2") may appear in the menu to allow for selection at the display device 102 (e.g., by way of a checkbox beside the name). The menu may then provide a confirmatory user interface control such as 'OK' button 630 to confirm that connection parameters are to be provided to the receiving device(s) 106 with the selected device identifier 625.

Referring again back to FIG. 5, the method may then proceed to act 220 where the display device 102 may use the secondary communications protocol to provide the link-layer connection parameters to the selected receiving device(s) 106. The receiving device 106 may use the second communications protocol to receive the connection parameters (act 222). The receiving device 106 may then, using the connection parameters received at act 222, proceed to request and form a second link-layer connection 108B (as shown in FIG. 1) with the ultrasound imaging machine 104 (acts 224-232). The ultrasound machine 104 may then transmit, and the receiving device 106 may receive, the ultrasound image feed (acts 234-236). These acts may be performed in a manner similar to what was described above in relation to FIG. 2.

Referring to FIG. 7, shown there generally as 700 is a flowchart diagram for acts of establishing a secondary connection at an ultrasound imaging machine 104 by providing connection parameters over a second communications protocol, according to at least one embodiment of the present disclosure. FIG. 7 is similar to the embodiment of FIG. 5 in that the connection parameters for the receiving device 106 to establish a link-layer connection with the ultrasound imaging machine 104 is provided by the display device 102 via a secondary communications protocol. However, unlike the method of FIG. 5, the display device 102 advertises its ability to provide connection parameters instead of the receiving device 106 advertising its ability to receive the connection parameters.

In FIG. 7, acts 202-216 may be performed in a manner similar what is described above with respect to FIG. 2. Similar to FIG. 5, in FIG. 7, act 218 from FIG. 2 has also been omitted for ease of reference. At act 705, the display device 102 may, using a second communications protocol, advertise its ability to provide connection parameters that allow a receiving device 106 to connect to the ultrasound imaging machine 104.

Figure 8:
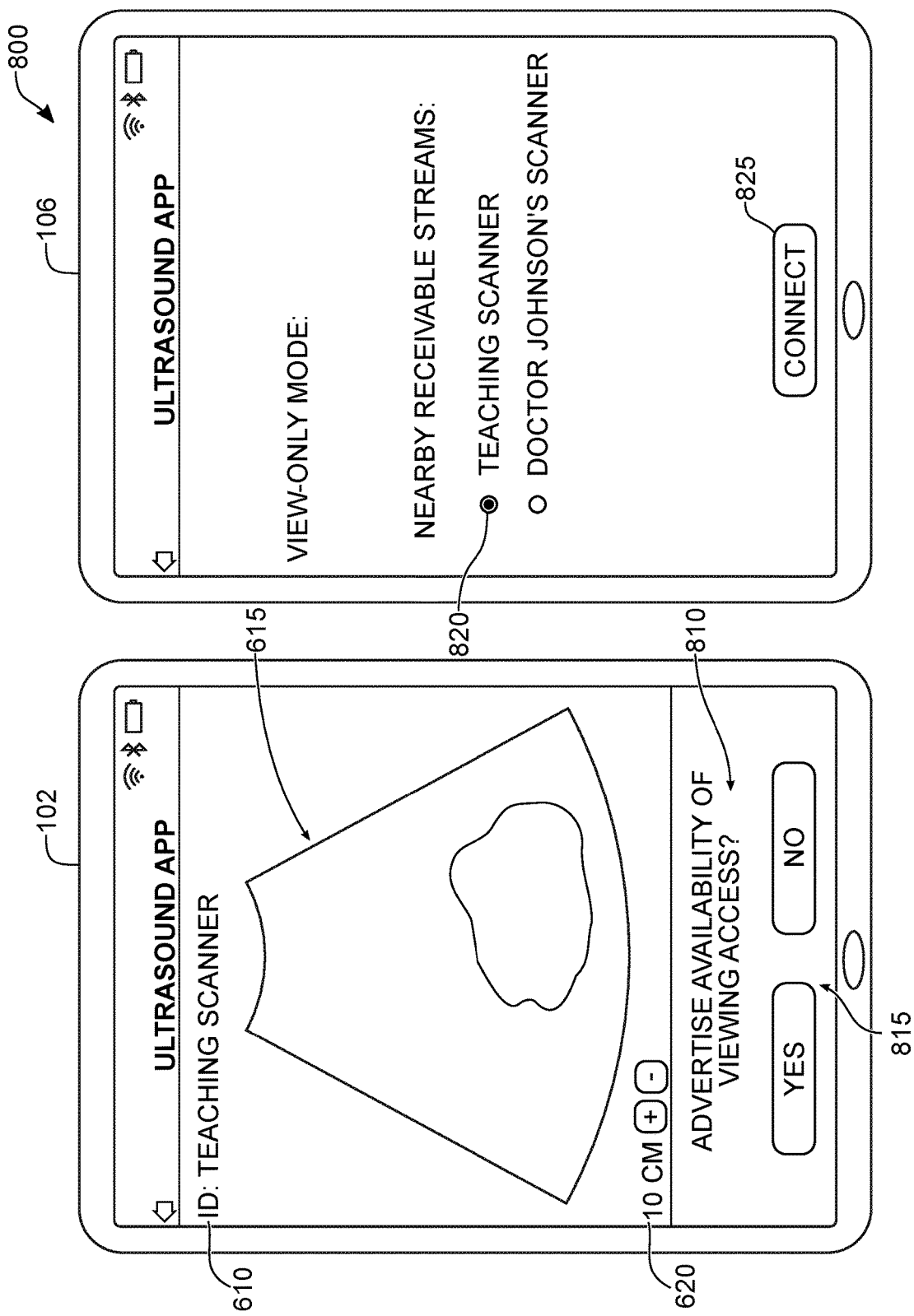

Referring also to FIG. 8, shown there generally as 800 are example user interfaces on a multi-use display device 102 and a receiving device 106 that allow the receiving device 106 to obtain connection parameters over a second communications protocol, according to at least one embodiments of the present disclosure. As illustrated in FIG. 8, the display device 120 shows an ultrasound image feed 615 with imaging depth controls 620. Also shown is an identifier 610 for the ultrasound imaging machine 104 that the display device 102 is controlling (e.g., "Teaching Scanner"). When configured to advertise the availability of the display device 102 to provide connection parameters to a receiving device 106, it may display user interface elements 810 that can receive user input to confirm. User input may be received using 'Yes' or 'No' buttons 815, for example. If a 'Yes' input is received, the display device 102 may advertise its ability to provide connection parameters using a second communications protocol (e.g., Bluetooth™) different from the first communications protocol (e.g., Wi-Fi™) used for the primary connection with the ultrasound imaging machine 104.

Referring again to FIG. 7, the method may then proceed to act 710. At act 710, the receiving device 106 may, using the second communications protocol, determine availability of the display device 102 to provide the connection parameters.

Referring again also to FIG. 8, the receiving device 106 may execute an ultrasound application in a view-only mode that performs act 710. In doing so, the receiving device 106 may provide an example user interface such as is shown on receiving device 106 in FIG. 8. For example, using the second communications protocol, the receiving device 106 may determine that the display device 102 is advertising its ability to provide connection parameters for the scanner with identifier "Teaching Scanner". This may result in the receiving device 106 displaying a user interface control showing "Nearby receivable streams" that lists available nearby devices 102 advertising their ability to provide connection parameters. As shown, the "Teaching Scanner" is shown along with another ultrasound imaging machine 104 with identifier "Doctor Johnson's Scanner". The user interface on receiving device 106 may further provide user interface controls 820 to select the ultrasound machine 104, and once selected, an option (e.g., "Connect" button 825) to confirm.

Referring back to FIG. 7, after act 710, the receiving device 106 may establish a connection 108C (as shown in FIG. 1) with the display device 102 using the second communications protocol. The establishment of this connection 108C may involve the exchange of additional messages between display device 102 and receiving device 106, which are not shown herein. Using this connection 108C, the display device 102 may proceed to act 220 to provide the link-layer connection parameters over the second communications protocol. The link-layer connection parameters may be received at the receiving device 106 (act 222). Acts 224-236 of FIG. 7 may then be performed in a manner similar to what was described above for the similarly-numbered acts in FIGS. 2 and 5.

Referring to FIG. 9, shown there generally as 900 is a flowchart diagram for acts of establishing a secondary connection at an ultrasound imaging machine by providing connection parameters over a second communications protocol, according to at least one embodiment of the present disclosure. FIG. 9 illustrates a further example embodiment of how a receiving device 106 may receive connection parameters over a second communications protocol that is different from a first communications protocol used to establish a primary communication link between an ultrasound imaging machine 104 and display device 102.

In the method of FIG. 9, the ultrasound imaging machine 104 may form a first link-layer connection with a multi-use display device 102, the first link-layer connection being for receiving commands that control imaging parameters of the ultrasound image feed. As with the embodiments described above in relation to FIGS. 5 and 7, this first link-layer connection is formed using a first communications protocol (e.g., Wi-Fi™). For ease of illustration, 202-212 formerly shown in FIGS. 5 and 7 are omitted in FIG. 9. Acts 214 and 216 may then be performed so that commands may be transmitted from the display device 102, and the ultrasound image feed may correspondingly be updated at the ultrasound imaging machine 104 for transmission to the display device 102.

At 905, the ultrasound imaging machine 104 may, using a second communications protocol, advertise availability for it to provide connection parameters to a receiving device 106. Since a first communications protocol (e.g., Wi-Fi™) is already used to establish a primary connection 108A with the display device 102, using a second communications protocol (e.g., Bluetooth™) different from the first communications protocol may allow the availability of the connection parameters to be advertised without disrupting the existing connection between the ultrasound imaging machine 104 and the display device 102.

At 910, the receiving device 106 may, using the second communications protocol, determine the availability of the ultrasound imaging machine 104 to provide the connection parameters, so as to establish a wireless connection with the ultrasound imaging machine 104 using the second communications protocol.

Referring again to FIG. 8, when the receiving device 106 determines the availability of the ultrasound imaging machine 104 to provide the connection parameters, the receiving device 106 may be configured to provide a user interface similar to what is shown on receiving device 106 of FIG. 8. For example, even if the ultrasound imaging machine 104 is advertising the availability of connection parameters (instead of the display device 102), the ultrasound imaging machine 104 may do so in a similar manner (e.g., providing its scanner identifier "Teaching Scanner"). From the perspective of the receiving device 106, it may not matter which device (e.g., the display device 102 or the ultrasound imaging machine 104) advertises the availability of the connection parameters, so long as it uses the same communications protocol (e.g., Bluetooth™). The appearance of the user interface on the receiving device 106 may thus be similar to what is shown in receiving device 106 of FIG. 8 in that a scanner with identifier "Teaching Scanner" may appear, even though the source of the advertisement may be from the ultrasound imaging machine 104 instead of the display device 102.

Referring back to FIG. 9, a narrow-bandwidth wireless communications link may be formed between the ultrasound imaging machine 104 and the receiving device 106 using the second communications protocol. At act 918, the ultrasound imaging machine 104 may then provide, using the second communications protocol, the link-layer connection parameters for establishing a higher-bandwidth connection that allows the receiving device 106 to receive the ultrasound image feed. These link-layer connection parameters may be received at act 222.

At act 224, the receiving device 106 may, using the connection parameters, send a request over the first communications protocol (e.g., with the higher bandwidth) to form a link-layer connection with the ultrasound imaging machine 104. For example, as discussed above, this may involve the receiving device 106 joining a WLAN network having the SSID being broadcasted by the ultrasound imaging machine 104. This request may be received at the ultrasound imaging machine 104 (act 226). Acts 228-236 may then proceed in a manner similar to how corresponding acts in the methods of FIGS. 2, 5, and 7 were described above.

In some embodiments, the ultrasound imaging machine may be configured to establish a secondary connection with the receiving device 106 automatically. For example, in embodiments where the same application allows a multi-use display device to operate as both a controlling device 102 and a receiving device 106 (e.g., the application can be configured to operate in both a regular mode and a view-only mode, as discussed above), the application may require a user to enter login credentials prior to permitting use of the application. In some embodiments, the user credentials may be associated with a user profile which, in turn, may be associated with an institution profile.

For example, an institution profile may refer to a hospital, clinic, medical practice, or any other collection of users (or single user). In such embodiments, when the ultrasound imaging machine 104 and/or the display device 102 advertises its availability to provide connection parameters, it may also include information related to the institution profile that the ultrasound machine 104 and/or the user profile of a logged-in user of the display device 102 is associated with. Additionally or alternatively, the receiving device 106 may communicate with an external web server to lookup the institution affiliation status of the ultrasound machine 104 and/or the user profile of a logged-in user at the display device 102 associated with an identifier provided in the advertisement message(s).

When the institution profile information is received at the receiving device 106, it may determine whether the logged-in user at the receiving device 106 belongs to the same institution. If so, the receiving device 106 may be configured to automatically receive the connection parameters and connect to the ultrasound imaging machine 104 without additional user input being required at the receiving device 106.

Similarly, if the receiving device 106 is configured to advertise its ability to receive the ultrasound image feed, it may include institution information in its advertisement information. Additionally or alternatively, the display device 102 (or other recipient) of the advertisement information may communicate with an external server to lookup the institution information for a logged-in user at the receiving device 106. If the controlling display device 102 determines that the receiving device 106 is associated with the same institution of a logged-in user of the controlling device 102, it may provide the connection parameters to the receiving device 106 which in turn may allow the receiving device 106 to connect to the ultrasound imaging machine 104 automatically.

In addition to facilitating ease of connection, the checking of whether the receiving device 106 is associated with the same institution profile as the ultrasound imaging machine 104 and/or the controlling display device 102 may enhance security. For example, enhanced security may be achieved by prohibiting an unauthorized receiving device 106 (e.g., that is not associated with the same institution profile) from receiving an ultrasound image feed. Additional information related to how an ultrasound imaging machine 104 can be secured for use by an institution affiliation status can be found in Applicant's U.S. patent application Ser. No. 15/786,279 filed Oct. 17, 2017 entitled "Systems and Methods for Securing Operation of an Ultrasound Scanner", the entire contents of which are hereby incorporated by reference.

Figure 10:
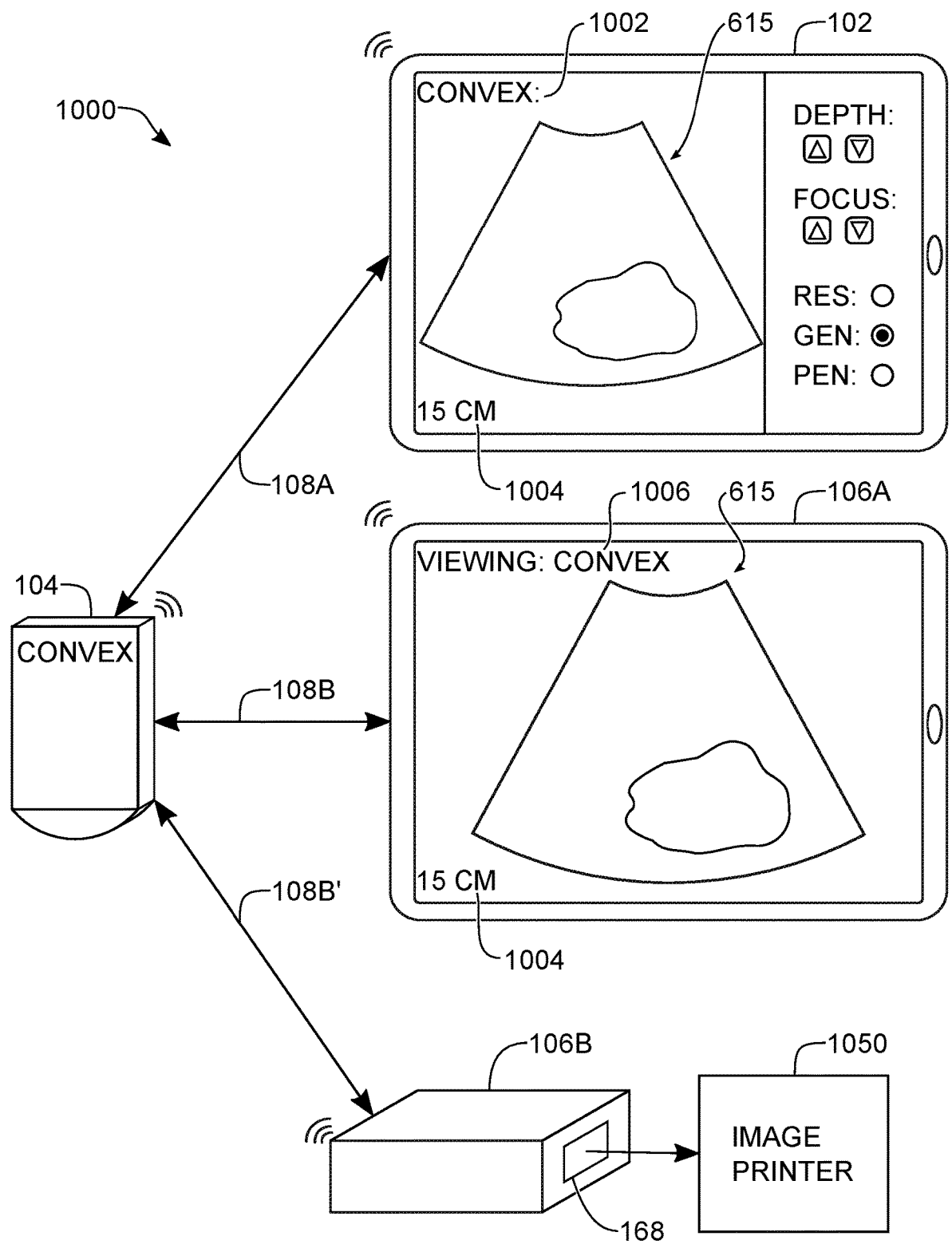
FIG. 10 is a diagram showing an ultrasound imaging machine having a first link-layer connection for receiving commands that control an ultrasound image feed, and multiple second link-layer connections for providing access to the ultrasound image feed, according to at least one embodiment of the present disclosure.

Referring to FIG. 10, shown there generally as 1000 is a diagram showing an ultrasound imaging machine 104 having a first link-layer connection for receiving commands that control an ultrasound image feed, and multiple second link-layer connections for receiving access to the ultrasound image feed, according to at least one embodiment of the present disclosure.

In the example embodiment shown in FIG. 10, the ultrasound imaging machine 104 is provided in the form of a handheld ultrasound scanner. For example, as shown, the scanner 104 is labeled "Convex". Operation of the ultrasound imaging machine 104 may be controlled by a display device 102 via a communication link 108A. As illustrated, the display device 102 may provide user interface controls for controlling imaging parameters of the ultrasound image feed being generated at the ultrasound imaging machine 104. For example, as shown, the controls illustrated are for modifying imaging depth, focus, and frequency (e.g., "resolution" (RES), "general" (GEN), and "penetration" (PEN) settings). Also shown in the user interface of display device 102 is the ultrasound image feed 615, an identifier 1002 of the ultrasound imaging machine 104, and an imaging depth 1004.

FIG. 10 also illustrates the presence of multiple types of receiving devices 106: a receiving device 106A that is another multi-use display device, and a dongle 106B. When a second link-layer connection 108B is established between the ultrasound imaging machine 104 and the receiving device 106A, the receiving device 106A can also display the ultrasound image feed that is being controlled from the display device 102. As shown, the user interface may be configured to be in a "viewing" mode 1006 that shows the identifier 1002 (e.g., "Convex") of the ultrasound imaging machine 104 that is generating the received ultrasound image feed 615. Various characteristics of the ultrasound image feed 615 may also be displayed, such as the imaging depth 1004. However, since the receiving device 106A only receives the ultrasound image feed for display (without providing the ability to control imaging parameters at the ultrasound imaging machine 104), the user interface at the receiving device 106A may not have the user interface controls that are shown in the user interface of the display device 102.

As noted above, in some embodiments, the ultrasound image feed being transmitted from the ultrasound machine 104 may be in a pre-scan converted format, such that scan conversion can take place at the destination device (e.g., either display device 102 and/or receiving device 106). This may allow the same ultrasound image feed to be displayed on receiving devices 106 of different visual formats.

Referring still to FIG. 10, while no controls for controlling imaging parameters are provided at a receiving device 106A, the receiving device 106A may still provide controls for manipulating how an ultrasound image feed can be viewed. For example, these controls may include flipping the ultrasound image along an axis (e.g., either vertical or horizontal), and/or zooming in on a region of the ultrasound image feed using a read zoom operation that allows magnification of a part of the image using existing image data (but without requiring an updating of the imaging parameters like a wrote zoom operation).

In various embodiments, an ultrasound imaging machine 104 may simultaneously form second link-layer connections with multiple receiving devices 106. For example, as illustrated, the ultrasound imaging machine 104 may also form a second link-layer connection 108B' with a receiving device 106B that is a dongle (not shown to scale in FIG. 10).

For example, the dongle 106B may have a port 168 for connecting an image output device. One or more ultrasound images from the ultrasound image feed received at the receiving device 106B may be provided to the image output device via the port 168. The image output device may be any suitable device that can receive or process one or more images from an ultrasound image feed. For example, an image output device may be a monitor (e.g., a simple display without any accompanying software for establishing a second-link layer connection 108B directly with the ultrasound imaging machine 104) or an ultrasound image printer 1050. In an example embodiment, the ultrasound image printer 1050 may be a Sony™ UP-897MD analog video printer that is designed for use with medical diagnostic equipment, such as ultrasound systems. The port 168 may be provided in any form suitable for connecting to the image output device. For example, the port 168 may be any type of present or future Universal Serial Bus (USB) connector, a MiniDisplay™ port, a High-Definition Multimedia Interface (HDMI) port, and/or analog audio/video connectors. In various embodiments, a dongle 106B may have multiple ports 168.

The dongle 106B may contain suitable electronics and/or software instructions for performing acts described herein as being performed by a receiving device 106. In certain instances where the dongle 106B is connected to an image output device that is not suitable for processing all the images in an ultrasound image feed, the software may be configured to process a marking signal that marks one or more ultrasound images from the ultrasound image feed that is being received by the dongle 106B. For example, in embodiments where the image output device is an image printer 1050, the marked one or more ultrasound images may be sent to the printer 1050 for printing.

The marking signal may be provided to the receiving device 106B in a variety of ways. For example, the marking signal may be received at the display device 102 controlling the imaging parameters of the ultrasound image feed. As that ultrasound image feed 615 is being displayed, user input may be received that marks a certain displayed image. The signal may then be transmitted as a command to the ultrasound imaging machine 104, so that the ultrasound image feed may include the marking signal when transmitting the ultrasound image feed to the receiving device 106B. By including the marking signal with the transmission of the ultrasound image feed, the receiving device 106B can, based on the signal, mark the one or more ultrasound images for providing to the image output device (e.g., image printer 1050) via the port 168.

In another example embodiment, the marking signal may be transmitted directly from the display device 102 to the receiving device 106B. For example, in the embodiments described above in relation to FIGS. 5-8 where a communications link 108C (as shown in FIG. 1) is established between the display device 102 and the receiving device 106B to allow the display device 102 to provide connection parameters to the receiving device 106B, this communications link 108C may be used also to transmit the marking signal. Once the marking signal is received, the receiving device 106B may mark the one or more ultrasound images for providing to the ultrasound output device (e.g. image printer 1050) via the port 168.

The marking signal may be implemented in various ways. For example, a field or flag may be reserved in the metadata of each frame of the ultrasound image feed for indicating when the marking signal has been activated. Additionally or alternatively, each frame of the ultrasound image feed may be provided with a frame number, and the marking signal may indicate the frame number(s) of the one or more image frames to be provided to the image output device. However, these implementations may require modification of the software instructions for generating and receiving of the ultrasound image feed.

In a further example embodiment, the marking signal may be implemented as an interrupt signal such that when the receiving device 106B receives the signal, it simply marks the current image frame being processed by the receiving device 106B when the signal is received. In situations where the receiving device 106B and the ultrasound machine 104 are all using a local network communications protocols (e.g., Wi-Fi™ and/or Bluetooth™), any latency due to transmission of the marking signal may be minimal. Also, the effect of any latency may not be noticed because it may be common for the ultrasound imaging machine 104 to be in a freeze mode such that a constant ultrasound image is being transmitted in the ultrasound image feed. Implementation of the marking signal this way may allow for greater ease of implementation since the software instructions related to the generation and transmission of the ultrasound image feed may not need be modified.

In some embodiments, a controlling device 102 may be able to input highlights and/or other annotations on an ultrasound image that also appears at the receiving device 106A. In some embodiments, such highlighting or annotation information may be transmitted directly from the controlling display device 102 to the receiving device 106A. For example, this information may be associated with either pre-scan converted ultrasound image data in polar coordinates and/or post-scan converted ultrasound image data in cartesian coordinates. Once this information is received at the receiving device 106A, it may be displayed (e.g., to highlight a target object in the ultrasound image feed 615). For example, such feature may be desirable in situations where a certain structure within the ultrasound image feed 615 is desired to be highlighted or annotated for viewing at the receiving device 106A. In various embodiments, the highlighting or annotation information may be transmitted from the display device 102 to the receiving device 106A using the same mechanisms described above for the marking signal.

Figure 11:
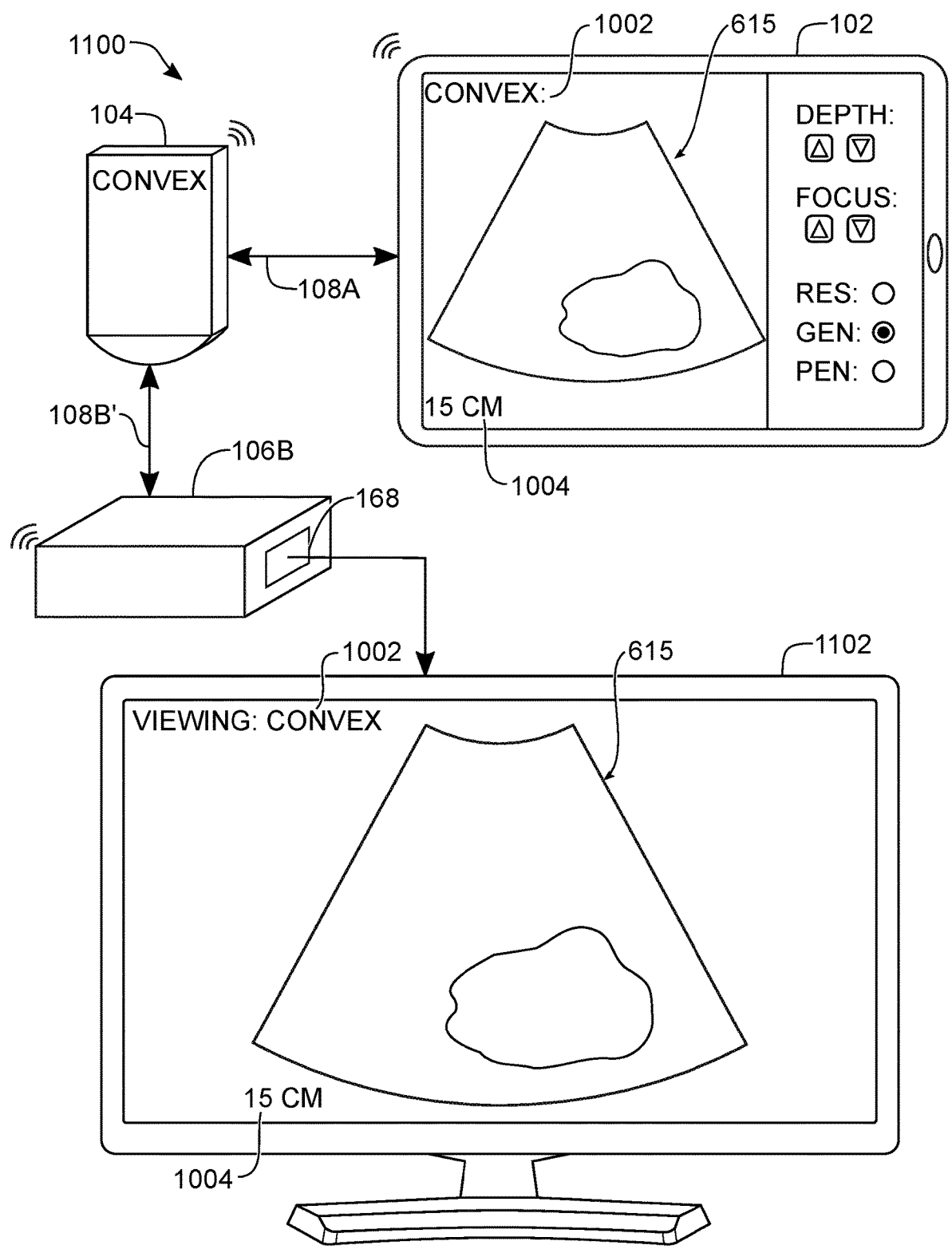
FIG. 11 is a diagram showing an ultrasound imaging machine having a first link-layer connection for receiving commands that control an ultrasound image feed, and a second link-layer connection with a receiving device having a port connected to a simple display, according to at least one embodiment of the present disclosure.

Referring to FIG. 11, shown there generally as 1100 is a diagram with an ultrasound imaging machine 104 having a first link-layer connection for receiving commands that control an ultrasound image feed, and a second link-layer connection with a receiving device 106B having a port 168 connected to a simple display, according to at least one embodiment of the present disclosure. The diagram of FIG. 11 is similar to that shown in FIG. 10, except that the receiving device 106A is not shown, and the dongle receiving device 106B is connected to a simple display 1102 instead of an image printer 1050.

A simple display may be any display without the ability to easily load and/or execute software that performs the acts described herein as being performed by a receiving device 106. For example, a simple display may be a traditional analog television that takes analog audio/video inputs. In this case, the port 168 on the dongle 106B may provide corresponding analog audio/video outputs so that it can be connected to the display. In another example, the display 1102 may be a more modern digital television without any "smart" capabilities. Such a display may have an HDMI input, and be connected to an embodiment of the dongle 106B with an HDMI port 168. A further example of a simple display 1102 may be a television pre-loaded with applications that allow it to access multimedia content from the Internet, but that does not have any straightforward, user-accessible way to load software that can execute acts performed by the receiving device 106 as described herein.

These types of simple displays 1102 may be commonplace in many hospitals and clinics. Configuring a dongle 106B to be able to connect to these displays 1102 to display an ultrasound image feed may be desirable to allow a larger audience to see the ultrasound image feed being generated at the ultrasound imaging machine 104.

As shown in FIG. 11, there is a controlling viewing device 102 with a primary connection 108A to ultrasound imaging machine 104. FIG. 11 also shows the ultrasound image feed 615 being controlled by controlling device 102, the imaging depth 1004 and the identifier 1002 for the ultrasound imaging machine 104. The ultrasound imaging machine 104 may form a secondary connection 108B' with the dongle 106B which can be connected via port 168 to the simple display 1102. In operation, the ultrasound image feed 615 can also be shown on the simple display 1102. In the illustrated example, the identifier 1002 for the ultrasound imaging machine 104 and the imaging depth 1004 may also be shown on the simple display 1102. In an example embodiment, scan conversion may take place at the receiving device 106B so as to convert the ultrasound image feed to be in a format suitable for viewing on the simple display 1102 (which may have a different resolution and/or aspect ratio compared to the controlling display device 102).

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are:

one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method of providing security for view access of an ultrasound image feed generated at an ultrasound imaging machine, the method comprising, at a multi-use display device:
    forming a first connection with the ultrasound image machine, the first connection being for transmitting commands that control imaging parameters of the ultrasound image feed, wherein the first connection is formed by a first application executing on the multi-use display device and the first application is associated with a first institution profile;
    determining connection parameters that allow the ultrasound imaging machine to form a second connection with a receiving device that is different from the multi-use display device;
    providing the connection parameters to the receiving device, wherein the connection parameters are received by a second application executing on the receiving device, and the second application is associated with a second institution profile, and wherein the receiving device:
        determines if the second institution profile corresponds to the first institution profile, and
        if the second institution profile corresponds to the first institution profile, the receiving device forms the second connection with the ultrasound imaging machine using the connection parameters, the second connection being used for receiving, at the receiving device, the ultrasound image feed controlled by the multi-use display device.

2. The method of claim 1, wherein prior to the providing of the connection parameters to the receiving device, the method further comprises the multi-use display device advertising information related to the first institution profile to the receiving device.

3. The method of claim 1, wherein the first institution profile associated with the first application is based on a logged-in user profile being used with the first application.

4. The method of claim 3, wherein prior to the providing of the connection parameters to the receiving device, the method further comprises the multi-use display device advertising information related to the logged-in user profile to the receiving device, and the receiving device communicating with a server to lookup the first institution profile of the logged-in user profile being used with the first application.

5. The method of claim 1, wherein the first institution profile associated with the first application is based on an association of the ultrasound imaging machine with the first institution profile.

6. The method of claim 5, wherein prior to the providing of the connection parameters to the receiving device, the method further comprises the multi-use display device advertising an identifier for the ultrasound imaging machine to the receiving device, and the receiving device communicating with a server to lookup the first institution profile associated with the identifier for the ultrasound imaging machine.

7. The method of claim 1, wherein the receiving device comprises a dongle having a port for connecting an image output device, wherein one or more ultrasound images from the ultrasound image feed received at the receiving device is provided to the image output device via the port.

8. The method of claim 1, wherein the first connection is formed using a first communications protocol, and prior to providing the connection parameters to the receiving device, the method further comprises:
determining availability of a receiving device to receive the ultrasound image feed, the determining being performed using a second communications protocol different from the first communications protocol,
wherein the providing the connection parameters is performed over the second communications protocol.

9. The method of claim 1, wherein the first connection is formed using a first communications protocol, and prior to providing the connection parameters to the receiving device, the method further comprises:
advertising availability of the multi-use display device to provide the connection parameters, the advertising being performed using a second communications protocol different from the first communications protocol,
wherein the providing the connection parameters is performed over the second communications protocol.

10. The method of claim 9, wherein the first communications protocol comprises a Wi-Fi™ protocol, and the second communications protocol comprises a Bluetooth™ protocol.

11. A method of providing security for view access of an ultrasound image feed generated at an ultrasound imaging machine, the method comprising, at the ultrasound imaging machine:
forming a first connection with a multi-use display device, the first connection being for receiving commands that control imaging parameters of the ultrasound image feed, wherein the first connection is formed with a first application executing on the multi-use display device and the first application is associated with a first institution profile, and wherein the multi-use display device:
determines connection parameters that allow the ultrasound imaging machine to form a second connection with a receiving device that is different from the multi-use display device, and
provides the connection parameters to the receiving device, wherein the connection parameters are received by a second application executing on the receiving device, and the second application is associated with a second institution profile, and wherein the receiving device:
determines if the second institution profile corresponds to the first institution profile, and
if the second institution profile corresponds to the first institution profile, transmits a request to the ultrasound imaging machine to form the second connection using the connection parameters;
based on the connection parameters, receiving the request from the receiving device to form the second connection;
forming the second connection with the receiving device; and
providing viewing access of the ultrasound image feed to the receiving device using the second connection.

12. The method of claim 11, wherein the first institution profile associated with the first application is based on an association of the ultrasound imaging machine with the first institution profile.

13. The method of claim 12, wherein prior to the providing of the connection parameters to the receiving device, the multi-use display device advertises an identifier for the ultrasound imaging machine to the receiving device, and the receiving device communicates with an external server to lookup the first institution profile associated with the identifier for the ultrasound imaging machine.

14. A method of providing security for view access of an ultrasound image feed generated at an ultrasound imaging machine, the method comprising, at a receiving device having no connection with the ultrasound imaging machine:
determining connection parameters from one of: the ultrasound imaging machine or a multi-use display device, the multi-use display device being different from the receiving device, wherein the ultrasound imaging machine has a first connection with the multi-use display device, and the first connection is for the multi-use display device to transmit commands to the ultrasound imaging machine to control imaging parameters of the ultrasound image feed, and wherein the first connection is formed by a first application executing on the multi-use display device and the first application is associated with a first institution profile, and wherein the determining of the connection parameters is performed by a second application executing on the receiving device, and the second application is associated with a second institution profile;
determining if the second institution profile corresponds to the first institution profile;
if the second institution profile corresponds to the first institution profile, based on the connection parameters, sending a request to the ultrasound imaging machine for the ultrasound imaging machine to form a second connection with the receiving device;
forming the second connection with the ultrasound imaging machine; and
receiving, via the second connection, the ultrasound image feed generated at the ultrasound imaging machine.

15. The method of claim 14, wherein prior to the determining of the connection parameters, the method further comprises the receiving device:
advertising an ability of the receiving device to receive the ultrasound image feed; and
advertising, to the ultrasound imaging machine or the multi-use display device, information related to the second institution profile.

16. The method of claim 15, wherein the ultrasound imaging machine or the multi-use display device communicates with a server to lookup the second institution profile being used with the second application, and wherein the ultrasound imaging machine or the multi-use display device determines if the first institution profile corresponds to the second institution profile prior to the connection parameters being determined by the receiving device.

17. The method of claim 14, wherein the second institution profile associated with the second application is based on a logged-in user profile being used with the second application executing on the receiving device.

18. The method of claim 17, wherein prior to the determining of the connection parameters, the method further comprises the receiving device:

advertising, to the ultrasound imaging machine or the multi-use display device, information related to the logged-in user profile, and wherein the ultrasound imaging machine or the multi-use display device communicates with a server to lookup the second institution profile of the logged-in user profile being used with the second application executing on the receiving device, and wherein the ultrasound imaging machine or the multi-use display device determines if the first institution profile corresponds to the second institution profile prior to the connection parameters being determined by the receiving device.

19. The method of claim 14, wherein the receiving device comprises a dongle having a port for connecting an image output device, and wherein the method further comprises:
   providing one or more ultrasound images from the ultrasound image feed received at the receiving device to the image output device via the port.

20. The method of claim 19, wherein the image output device comprises at least one of: an ultrasound image printer and a simple display.

* * * * *